US010648965B2

(12) United States Patent
Feng et al.

(10) Patent No.: US 10,648,965 B2
(45) Date of Patent: May 12, 2020

(54) MOLECULAR SENSING DEVICE

(71) Applicant: ECOLE POLYTECHNIQUE FEDERALE DE LAUSANNE (EPFL), Lausanne (CH)

(72) Inventors: Jiandong Feng, Hangzhou (CN); Ke Liu, Chavannes-prés-Renens (CH); Aleksandra Radenovic, St. Sulpice (CH)

(73) Assignee: École Polytechnique Fédérale de Lausanne (EPFL), Lausanne (CH)

( * ) Notice: Subject to any disclaimer, the term of this patent is extended or adjusted under 35 U.S.C. 154(b) by 474 days.

(21) Appl. No.: 15/118,957

(22) PCT Filed: Feb. 13, 2015

(86) PCT No.: PCT/EP2015/053042
§ 371 (c)(1),
(2) Date: Nov. 21, 2016

(87) PCT Pub. No.: WO2015/121394
PCT Pub. Date: Aug. 20, 2015

(65) Prior Publication Data
US 2017/0059547 A1    Mar. 2, 2017

(30) Foreign Application Priority Data

Feb. 14, 2014  (EP) .................................... 14155254
Jul. 21, 2014  (EP) .................................... 14177908

(51) Int. Cl.
*G01N 33/487*  (2006.01)
*C12Q 1/6869*  (2018.01)
(Continued)

(52) U.S. Cl.
CPC ..... *G01N 33/48721* (2013.01); *C12Q 1/6869* (2013.01); *G01N 15/1031* (2013.01);
(Continued)

(58) Field of Classification Search
CPC ......... G01N 33/48721; G01N 15/1031; G01N 27/3278; G01N 27/44791; C12Q 1/6869;
(Continued)

(56) References Cited

U.S. PATENT DOCUMENTS

2010/0148126 A1* 6/2010 Guan .................. C07D 233/06
                                                        252/500
2011/0120890 A1* 5/2011 MacPherson .... G01N 33/48721
                                                        205/792

(Continued)

FOREIGN PATENT DOCUMENTS

WO   WO 2011/130312   10/2011
WO   WO 2012/073009   6/2012
WO   WO 2013/021815   2/2013

OTHER PUBLICATIONS

Branton, D. et al. "The potential and challenges of nanopore sequencing" *Nature Biotechnology*, Oct. 9, 2008, pp. 1146-1153, vol. 26, No. 10.

(Continued)

*Primary Examiner* — Maris R Kessel
(74) *Attorney, Agent, or Firm* — Saliwanchik, Lloyd & Eisenschenk

(57) ABSTRACT

Molecular sensing system including: a sensing device (5) comprising at least one support layer (10), and an active layer (6) mounted on said support layer and having at least one nano-pore (12) configured for translocation of a molecular analyte (18) therethrough; an electrically conducting liquid (4) in contact with the active layer in a region around said nano-pore; and a signal processing circuit (7) comprising an ionic current circuit (8) configured to generate and measure an ionic current (Ii) in the electrically conducting liquid influenced by the translocation of the molecular analyte through the nano-pore. The molecular sensing device of the invention allows for single-nucleotide dis- (Continued)

crimination and detection of the specific sequence within ssDNA.

15 Claims, 18 Drawing Sheets

(51) Int. Cl.
 G01N 27/447 (2006.01)
 G01N 15/10 (2006.01)
 G01N 15/00 (2006.01)
(52) U.S. Cl.
 CPC ............... *G01N 27/44791* (2013.01); *G01N 2015/0065* (2013.01)
(58) Field of Classification Search
 CPC ............... C12Q 2565/631; B82Y 5/00; B82B 1/00–008
 See application file for complete search history.

(56) References Cited

U.S. PATENT DOCUMENTS

| 2012/0234679 A1* | 9/2012 | Garaj | B82Y 30/00 204/520 |
| 2014/0021047 A1* | 1/2014 | Shim | G01N 27/44791 204/451 |
| 2014/0158540 A1* | 6/2014 | Ohura | G01N 33/48721 204/543 |

OTHER PUBLICATIONS

Carda-Broch, S. et al. "Solvent properties of the 1-butyl-3-methylimidazolium hexafluorophosphate ionic liquid" *Analytical and Bioanalytical Chemistry*, Jan. 4, 2003, pp. 191-199, vol. 375.
Chandran, A. et al. "Groove Binding Mechanism of Ionic Liquids: A Key Factor in Long-Term Stability of DNA in Hydrated Ionic Liquids?" *Journal of the American Chemical Society*, Nov. 26, 2012, pp. 20330-20339, vol. 134.
Chiappe, C. et al. "Ionic liquids: solvent properties and organic reactivity" *Journal of Physical Organic Chemistry*, 2005, pp. 275-297, vol. 18.
Clarke, J. et al. "Continuous base identification for single-molecule nanopore DNA sequencing" *Nature Nanotechnology*, Feb. 22, 2009, pp. 1-6.
Crosthwaite, J.M. et al. "Phase transition and decomposition temperatures, heat capacities and viscosities of pyridinium ionic liquids" *The Journal of Chemical Thermodynamics*, May 11, 2005, pp. 559-568, vol. 37.
Davenport, M. et al. "Squeezing Ionic Liquids through Nanopores" *Nano Letters*, 2009, pp. 2125-2128, vol. 9, No. 5.
De Zoysa, R.S.S. et al. "Slowing DNA Translocation through Nanopores Using a Solution Containing Organic Salts" *The Journal of Physical Chemistry B*, 2009, pp. 13332-13336, vol. 113, No. 40.
Di Fiori, N. et al. "Optoelectronic control of surface charge and translocation dynamics in solid-state nanopores" *Nature Nanotechnology*, Dec. 2013, pp. 946-951, vol. 8.
Feng, J. et al. "Identification of single nucleotides in $MoS_2$ nanopores" *Nature Nanotechnology*, Dec. 2015, pp. 1070-1077, vol. 10.
Fologea, D. et al. "Slowing DNA Translocation in a Solid-State Nanopore" *Nano Letters*, 2005, pp. 1734-1737, vol. 5, No. 9.
Garaj, S. et al. "Graphene as a subnanometre trans-electrode membrane" *Nature*, Sep. 9, 2010, pp. 190-194, vol. 467.
He, Y. et al. "Controlling DNA Translocation through Gate Modulation of Nanopore Wall Surface Charges" *American Chemical Society*, 2011, pp. 5509-5518, vol. 5, No. 7.
Keskin, S. et al. "A review of ionic liquids towards supercritical fluid applications" *Journal of Supercritical Fluids*, 2007, pp. 150-180, vol. 43.
Khupse, N.D. et al. "Temperature dependent viscosity of mixtures of ionic liquids at different compositions" *Indian Journal of Chemistry*, May-Jun. 2010, pp. 727-730, vol. 49A.
Kowalczyk, S.W. et al. "Modeling the conductance and DNA blockade of solid-state nanopores" *Nanotechnology*, 2011, pp. 1-5, vol. 22.
Liu, K.-K. et al. "Growth of Large-Area and Highly Crystalline $MoS_2$ Thin Layers on Insulating Substrates" *Nano Letters*, 2012, pp. 1538-1544, vol. 12.
Novoselov, K.S. et al. "Electric Field Effect in Atomically Thin Carbon Films" *Science*, Oct. 22, 2004, pp. 666-669, vol. 306.
Novoselov, K.S. et al. "Two-dimensional atomic crystals" *Proceedings of the National Academy of Sciences*, Jul. 25, 2005, pp. 10451-10453, vol. 102, No. 30.
Petrone, N. et al. "Chemical Vapor Deposition-Derived Graphene with Electrical Performance of Exfoliated Graphene" *Nano Letters*, May 14, 2012, pp. 2751-2754, vol. 12.
Radisavljevic, B. et al. "Small-signal amplifier based on a single-layer $MoS_2$" *Applied Physics Letters*, 2012, pp. 043103-1-043103-4, vol. 101.
Raillon, C. et al. "Fast and automatic processing of multi-level events in nanopore translocation experiments" *Nanoscale*, 2012, pp. 4916-4924, vol. 4.
Schneider, G.F. et al. "Tailoring the hydrophobicity of graphene for its use as nanopores for DNA translocation" *Nature Communications*, Oct. 15, 2013, pp. 1-7.
Seddon, K.R. et al. "Influence of chloride, water, and organic solvents on the physical properties of ionic liquids" *Pure and Applied Chemistry*, Jul. 2000, pp. 2275-2287, vol. 72, No. 12.
Storm, A.J. et al. "Fast DNA Translocation through a Solid-State Nanopore" *Nano Letters*, Jul. 2005, pp. 1193-1197, vol. 5, No. 7.
Traversi, F. et al. "Detecting the translocation of DNA through a nanopore using graphene nanoribbons" *Nature Nanotechnology*, Nov. 17, 2013, pp. 1-7.
Venkatesan, B.M. et al. "Nanopore sensors for nucleic acid analysis" *Nature Nanontechnology*, Sep. 18, 2011, pp. 1-10.
Yenta, K. et al. "Differentiation of Short, Single-Stranded DNA Homopolymers in Solid-State Nanopores" *American Chemical Society Nano*, 2013, pp. 4629-4636, vol. 7, No. 5.
Wanunu, M. et al. "DNA Translocation Governed by Interactions with Solid-State Nanopores" *Biophysical Journal*, Nov. 2008, pp. 4716-4725, vol. 95.
Wanunu, M. et al. "Electrostatic focusing of unlabeled DNA into nanoscale pores using a salt gradient" *Nature Nanotechnology*, Feb. 2010, pp. 160-165, vol. 5.
Wanunu, M. et al. "Rapid electronic detection of probe-specific microRNAs using thin nanopore sensors" *Nature Nanotechnology*, Nov. 2010, pp. 807-814, vol. 5.
Zhang, P. et al. "Ionic liquids with metal chelate anions" *Chemical Communications*, 2012, pp. 2334-2336, vol. 48.
Written Opinion in International Application No. PCT/EP2015/053042, dated Jun. 29, 2015, pp. 1-7.

* cited by examiner

| Step | Process description | Cross-section after process |
|---|---|---|
| a | Substrate: Double Side polished, Boron-doped Si (100) wafers with resistivities of 20 - 30 -Ohm.cm<br><br>Thickness: $SiO_2$ 100 nm, low stress LPCVD<br><br>$SiO_x$: 60nm + $Si_3N_4$: 20 nm | 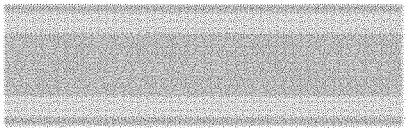 |
| b | Photolithography 1<br><br>PR: AZ1512HS on LOR, EVG150<br><br>Mask n. 1 on MA6 | 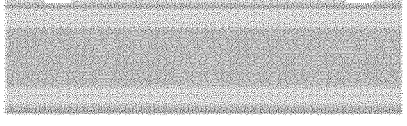 |
| c | Metal evaporation and lift-off<br><br>Machine: LAB 600<br><br>Material: Cr 10 nm / Pt 50 nm<br><br>E-beam markers and coordinate system |  |
| d | Photolithography 2<br><br>PR: AZ1512HS on LOR, EVG150<br><br>Mask n. 2 on MA6 | 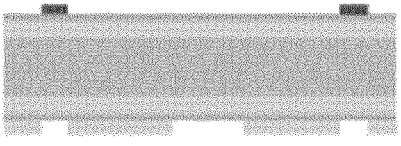 |
| e | *Dicing* |  |

Figure 10

| | | |
|---|---|---|
| f | KOH etching (done in LBEN)<br>Recipe: 6 h in 25 % KOH (250 g of salt in 1 l of DI water) @ 80 °C (84 °C on the bath controller) | |
| g | E-beam litho and RIE<br><br>Material: PMMA as photoresist<br>Window size 200nm to 500nm | |
| h | Monolayer MoS₂ fabrication<br>mechanically exfoliated or CVD<br>Done in LANES | |
| i | MoS₂ Transfer<br>PMMA<br>Done in LANES | |
| j | TEM drilling Pore<br><br>JEOL 2200FS TEM | |
| k | | |

MOLECULAR SENSING DEVICE

CROSS-REFERENCE TO RELATED APPLICATION

This application is the U.S. national stage application of International Patent Application No. PCT/EP2015/053042, filed Feb. 13, 2015.

FIELD OF THE INVENTION

The present invention pertains generally to the fields of molecular sensing, in particular solid-state sensing of biomolecules such as DNA, RNA and protein sensing and DNA, RNA sequencing.

BACKGROUND OF THE INVENTION

Solid-state nanopores have been developed in order to sense molecular analytes and in particular biomolecules such as DNA, RNA and proteins because they are viewed as being more robust and less dynamic than biopores which are based on protein (toxin)-lipid membrane systems (Clarcke et al., 2009, *Nat. Nanotechnol.*, 4, 265). Solid-state nanopores can operate in various liquid media and pH conditions and their production is scalable and compatible with nanofabrication techniques and can be integrated with other sensing methods that exploit tunneling or local potential gating.

The sensing principle is the same as in bio-engineered pores and ideally, the sequence of nucleotides, genetic information, along a single DNA molecule can be registered by monitoring small changes in the ionic current caused by the transient residing of single nucleotides within a nanometer size pore.

Before sequencing with solid state nanopores, three fundamental requirements on ionic or transverse current signals have to be met: spatial resolution in the order of few nucleotides, high signal to noise ratio to distinguish between signals related to different nucleotides and temporal resolution of the signal that allows acquiring enough points per nucleotide using state of the art current-voltage amplifier systems have to be achieved.

However, solid state nanopores exhibit a relatively lower single molecule detection sensitivity compared to biopores due to their intrinsic thickness and lack of control over surface charge distribution: temporal resolution of ionic current in solid state nanopores is on order of 10-50 base pairs/ms (Branton et al., 2008, *Nat. Nanotechnol.*, 26, 1146). Together with lower ionic current signal to noise ratio, relatively larger sensing region, which is due to the pore membrane thickness, has been major obstacle in achieving sequencing data when using solid state nanopores.

Recently, thin membranes have been proposed to extend the applications of solid-state nanopore to, e.g., detection of short DNA oligomers and differentiation of short nucleotides homopolymers (Venta et al., 2013, *ACS Nano*, 7, 4629-4636). Several groups have used monolayer graphene (thickness of ~0.35 nm) as a nanopore membrane for the detection of DNA translocation (Garaj et al., 2010, *Nature*, 467, 7312, 190-193) and simultaneous detection of DNA translocation with two synchronized signals, the ionic current in the nanopore and local potential change in the graphene nanoribbon transistor has been reported (Traversi et al., 2013, *Nat. Nanotechnol.*, 8, 939-945).

However, graphene nanopores exhibit strong hydrophobic interactions with DNA that limits their long-term use due to the clogging. Schneider et al. have implemented surface functionalization with pyrene ethylene glycol of graphene nanopores and demonstrated that this process prevents DNA absorption on graphene and renders graphene nanopores usable for extended periods of time (Schneider et al., 2013, *Nat. Commun.*, 4, 2619).

Several attempts have been carried-out for improving temporal resolution of translocating DNA molecules in solid-state nanopores, including using the DNA pore interactions, controlling the electrolyte parameters (temperature, salt concentration, viscosity), nanopore surface functionalization, change in nanopore surface charge though light-control and applying an electrical bias voltage across the nanopore to reduce the mobility of the DNA. Fologea et al. (Fologea et al., 2005, *Nano Lett*, 5, 1734) added glycerol into buffer to increase the viscosity and consequently reduce the mobility of DNA and by controlling the electrolyte temperature, salt concentration, viscosity, electrical bias voltage across the nanopore, obtained a 3 base/ms, but working with glycerol/water reduced the ionic current signal. In addition, the highest viscosity of the solution that they could use was 5.2 cP.

In conclusion, DNA translocations in biological nanopores are currently too slow, on the other hand in solid-state nanopores are too fast compared to the optimal DNA sequencing velocity of 1-50 nucleotide/ms (Venkatesan et al., 2011, *Nature Nanotechnology* 6: 615-624). So far achieved temporal resolution in solid-state nanopores is on order of 3000-50000 nt/ms (Branton et al., 2008, supra).

Therefore, there is a need for selective and sensitive sensing systems for analytes, in particular biomolecular analytes that allow a rapid analysis at the molecular levels such as for DNA, RNA and protein sequencing.

SUMMARY OF THE INVENTION

An object of this invention is to provide a system for sensing molecular analytes that enable accurate and reliable detection of the characteristics of analytes at the molecular level.

It is advantageous to provide a system where temporal resolution of the analyte detection is improved.

It is advantageous to provide a system where temporal resolution of the analyte detection is improved such that there is no need of prior manipulation on the analyte to ease detection (e.g. PCR amplification or cutting strands into pieces).

It is advantageous to provide a system for sensing molecular analytes that is economical to produce and to use.

It is advantageous to provide a system for sensing molecular analytes that has a high productivity, in particular that enables rapid detection of the characteristics of analytes at the molecular level.

It is advantageous to provide a system where analyte translocation, in particular DNA translocation through the pore(s) is reduced, while keeping acceptable signal to noise ratios and independently of the analyte length.

Objects of this invention have been achieved by providing a sensing system including a sensing device (5) comprising at least one support layer (10), and an active layer (6) mounted on said support layer and having at least one nano-pore (12) configured for translocation of a molecular analyte (18) therethrough; an electrically conducting liquid (4) in contact with the active layer in a region around said nano-pore; and a signal processing circuit (7) comprising an ionic current circuit (8) configured to generate an ionic current (Ii) in the electrically conducting liquid influenced by the translocation of the molecular analyte through the nano-pore, wherein said conducting liquid comprises a first conducting liquid (4a) on a first side of the active layer and a second conducting liquid (4b) on a second side of the active layer, the first conducting liquid having a viscosity (cP1) greater than a viscosity (cP2) of the second conducting liquid, wherein the first conducting liquid comprises a room temperature ionic liquid (RTIL).

Objects of this invention have been achieved by providing a sensing system including a sensing device (5) comprising at least one support layer (10) comprising a support layer orifice (14), and an active layer (6) mounted on said support layer and having at least one nano-pore (12) configured for translocation of a molecular analyte (18) therethrough, a diameter (Ds) of the support layer orifice being greater than a diameter (Dp) of the nano-pore, whereby a portion of the active layer extends over said support layer orifice in a suspended manner; an electrically conducting liquid (4) in contact with the active layer in a region around said nano-pore; and a signal processing circuit (7) comprising an ionic current circuit (8) configured to generate and measure an ionic current (Ii) in the electrically conducting liquid influenced by the translocation of the molecular analyte through the nano-pore, wherein at least said portion of the active layer extending over said support layer orifice in a suspended manner is of a semi-conducting material, and wherein the a signal processing circuit (7) further comprises a transverse current circuit (9) configured to generate a transverse current (It) in the semi-conducting material.

Disclosed herein, according to a first aspect of the invention, is a molecular sensing system including: a sensing device comprising at least one support layer, and an active layer mounted on said support layer and having at least one nano-pore configured for translocation of a molecular analyte therethrough; an electrically conducting liquid in contact with the active layer in a region around said nano-pore; and a signal processing circuit comprising an ionic current circuit configured to generate an ionic current in the electrically conducting liquid influenced by the translocation of the molecular analyte through the nano-pore, wherein said conducting liquid comprises a first conducting liquid on a first side of the active layer and a second conducting liquid on a second side of the active layer, the first conducting liquid having a viscosity greater than a viscosity of the second conducting liquid.

Disclosed herein, according to a second aspect of the invention, is a molecular sensing system including: a sensing device comprising at least one support layer comprising a support layer orifice, and an active layer mounted on said support layer and having at least one nano-pore configured for translocation of a molecular analyte therethrough, a diameter of the support layer orifice being greater than a diameter of the nano-pore, whereby a portion of the active layer extends over said support layer orifice in a suspended manner; an electrically conducting liquid in contact with the active layer in a region around said nano-pore; and a signal processing circuit comprising an ionic current circuit configured to generate an ionic current in the electrically conducting liquid influenced by the translocation of the molecular analyte through the nano-pore, wherein at least said portion of the active layer extending over said support layer orifice in a suspended manner is of a semi-conducting material, and wherein the a signal processing circuit further comprises a transverse current circuit configured to generate a transverse current in the semi-conducting material.

In an embodiment of the invention, the first conducting liquid comprises a room temperature ionic liquid (RTIL).

In an embodiment of the invention, the room temperature ionic liquid (RTIL) has a viscosity (cP1) at room temperature from about 100 centipoises (cP) to about 500 centipoises (cP), for instance from about 100 cP to about 300 cP.

In an embodiment of the invention, the room temperature ionic liquid (RTIL) is selected from an essentially pure RTIL, optionally mixed with an organic solvent, or a mixture of a water-miscible RTIL in water with a water content from about 5 to about 50 wt %.

In an embodiment of the invention, the room temperature ionic liquid (RTIL) is selected from a group based on the anion nature: (a) systems based on $AlCl_3$ and organic salts such as 1-butyl-3-methylimidazolium chloride, [bmim][Cl]; (b) systems based on anions like $[PF_6]^-$, $[BF_4]^-$ and $[SbF_6]^-$; (c) systems based on anions such as $[CF_3SO_3]^-$, $[(CF_3SO_2)_2N]^-$, $[Tf_2N]^-$ and similar; (d) systems based on anions such as alkylsulfates and alkylsulfonates; (e) carboranes ($[CB_{11}H_{12}]^-$ $[CB_{11}H_6Cl_6]^-$, $[CB_{11}H_6Br_6]^-$) and orthoborates.

In an embodiment of the invention, the room temperature ionic liquid (RTIL) comprises hexafluorophosphate anions.

In an embodiment of the invention, the room temperature ionic liquid (RTIL) includes N,N-dialkylimidazolium cations such as dibutyl, dioctyl, dinonyl, didecylimidazolium, 1-Butyl-3-methyl and 1-ethyl-3-methylimidazolium cations ([bmim]+ and [emim]+).

In another embodiment of the invention, the room temperature ionic liquid (RTIL) includes pyridinium cations such as 1-butyl pyridinium (bpy)$^+$ cations and the like such as described in Crosthwaite et al., 2005, *The Journal of Chemical Thermodynamics,* 37(6): 559-568.

In an embodiment of the invention, the room temperature ionic liquid (RTIL) comprises 1-Butyl-3-methyl and 1-ethyl-3-methyl imidazolium cations.

In an embodiment of the invention, the room temperature ionic liquid (RTIL) comprises 1-butyl pyridinium (bpy)$^+$ cation.

In an embodiment of the invention, the room temperature ionic liquid (RTIL) is preferably 1-butyl-3-methylimidazolinom hexafluorophosphate (BminPF$_6$) but in principle RTILs that have high viscosity but have cations that bind preferentially to A, T, G, U or C nucleotides could provide additional benefit in specificity such as described in Zhang et al., 2012, *Ionic liquids with metal chelate anions, Chemical Communications* 48: 2334-2336. These properties could be further exploited to amplify the small differences in bases.

In an embodiment of the invention, the second conducting liquid may advantageously comprise or consist in an aqueous liquid comprising an electrolyte.

In an embodiment of the invention, the electrolyte may be potassium chloride (KCl).

In an advantageous embodiment of the invention, the support layer comprises a support layer orifice, a diameter of the support layer orifice being greater than a diameter of the nano-pore, whereby a portion of the active layer extends over said support layer orifice in a suspended manner, and wherein at least said portion of the active layer extending over said support layer orifice in a suspended freestanding manner is of a semi-conducting material.

In an embodiment of the invention, the signal processing circuit further comprises a transverse current circuit configured to generate a transverse current (It) in the semi-conducting material.

In an embodiment the transverse current circuit comprises means to measure the transverse current configured to provide a signal used in the measurement of a characteristic of the molecular analyte as it displaces through the nanopore.

In another embodiment the transverse current circuit comprises means to amplify the measured transverse current.

In an embodiment the ionic current circuit comprises means to measure the ionic current configured to provide a signal used in the measurement of a characteristic of the molecular analyte as it displaces through the nano pore.

In an embodiment of the invention, the material of the active layer may advantageously be or comprise $MoS_2$.

In an embodiment of the invention, the material of the semi-conducting material may advantageously be $MoS_2$.

In an embodiment of the invention, the material of the support layer may comprise $SiN_x$.

In an embodiment of the invention, the ionic current circuit may be connected to a pair of Ag/AgCl electrodes coupled to the conducting liquid on opposite sides of the active layer.

The above mentioned features may be combined in any appropriate manner.

An advantageous characteristic of the invention is to provide a system with an atomic thick active layer that can have semi-conducting, conducting or superconductive (depending on the 2D material), having atomically thin membrane improves detection accuracy and reliability. The device can be integrated with transverse detection and this moreover allows providing a plurality of sensing pores in the active layer for measurement of a plurality of molecules in parallel.

An advantageous characteristic of the invention is to provide a system where the detection sensitivity is increased, notably by a decrease of the signal to noise is increased and enhancement of the ionic current signal. According to one aspect, differentiation between nucleotides in solid state pore (hundreds of pico Amperes (pA) in ionic current) is greatly enhanced compared to biological nanopore (tens of pA).

An advantageous characteristic of the invention is to provide a system where pore dimensions may be adjusted to the needs using a highly focused electron beam without the risk of damaging the active layer.

An advantageous characteristic of the invention is to provide a system where the atomically thick active layer is robust enough to avoid being supported by a support layer in the area of the active layer where the pore will be formed, therefore reducing the pore drilling time and improving pore characteristics such as size, shape, and edge properties.

An advantageous characteristic of the invention is to provide a system where the thickness of the nanopore(s) of the active layer is atomically thin.

An advantageous characteristic of the invention is to provide a system having an active layer where the pore diameter can be larger than its thickness.

An advantageous characteristic of the invention is to provide a system where adsorption of the analyte, in particular DNA analytes, onto the active surface is decreased or avoided without the need of additional surface treatments.

An advantageous characteristic of the invention is to provide a system where the viscosity of the conducting fluids can be tuned according to the needs and the analyte to be characterized. The viscosity gradient system exploits room temperature ionic liquid (preferably 1-butyl-3-methylimidazolium hexafluorophosphate (BmimPF6)) as solvent, allowing slowing down DNA translocation speed. This allows adjusting the speed of translocation and thus improving detection accuracy and reliability.

An advantageous characteristic of the invention is to provide a system for sensing molecular analytes that enable accurate and reliable detection of the characteristics of analytes at the molecular level having obtained optimal temporal, spatial resolution while keeping high signal to noise ratio.

In conventional solid state nanopores, analyte translocation speed is too fast to resolve each nucleotide (1-20 nt per μs). In biological pore, using enzyme to ratchet ssDNA base by base, the resulting speed (1-10 nt per s) is too slow for rapid sequencing. In the present invention one can obtain an optimal speed (10-50 nt per ms) for rapid DNA (1-80 h for whole human genome). The invention advantageously provides a system where temporal resolution of the analyte detection is improved such that there is no need of prior manipulation on the analyte to ease detection (e.g. PCR amplification or cutting strands into individual nucleotides).

An advantageous characteristic of the invention is to provide a system for sensing molecular analytes that is economical to produce and to use by means of nanofabrication and when CVD material is used.

An advantageous characteristic of the invention is to provide a system where analyte translocation, in particular DNA translocation through the pore(s) is reduced, while keeping acceptable signal to noise ratios and independently of the analyte length.

An advantageous characteristic of the invention is to provide a system for sensing molecular analytes that has a high productivity, scalability and integrability in particular that enables rapid detection of the characteristics of analytes at the molecular level with single nucleotide resolution.

Moreover, a molecular sensing system according to the invention could also pave the way to cheaper sensing devices by taking advantage of semiconductor manufacturing technology to mass-produce and shrink the costs for sequencers based on such sensing system.

Other features and advantages of the invention will be apparent from the claims, detailed description, and figures.

Density plot of single nucleotides in $MoS_2$ nanopore; for dAMP (c1), the position of the hot spot is (0.5, 0.65), for dTMP (c2), (0.09, 0.45), for dCMP (c3), (0.06. 0.32) and for dGMP (c4) (0.15, 0.8). The color-map at the right shows the normalized density distribution of events. Data acquired in pure RTIL cis chamber: 100 mM KCl, 25 mM Tris HCl, pH 7.5. The nucleotides' concentration in RTILs was 5 µg/ml. Insets show chemical 3D structure of nucleotides.

Figure 13:
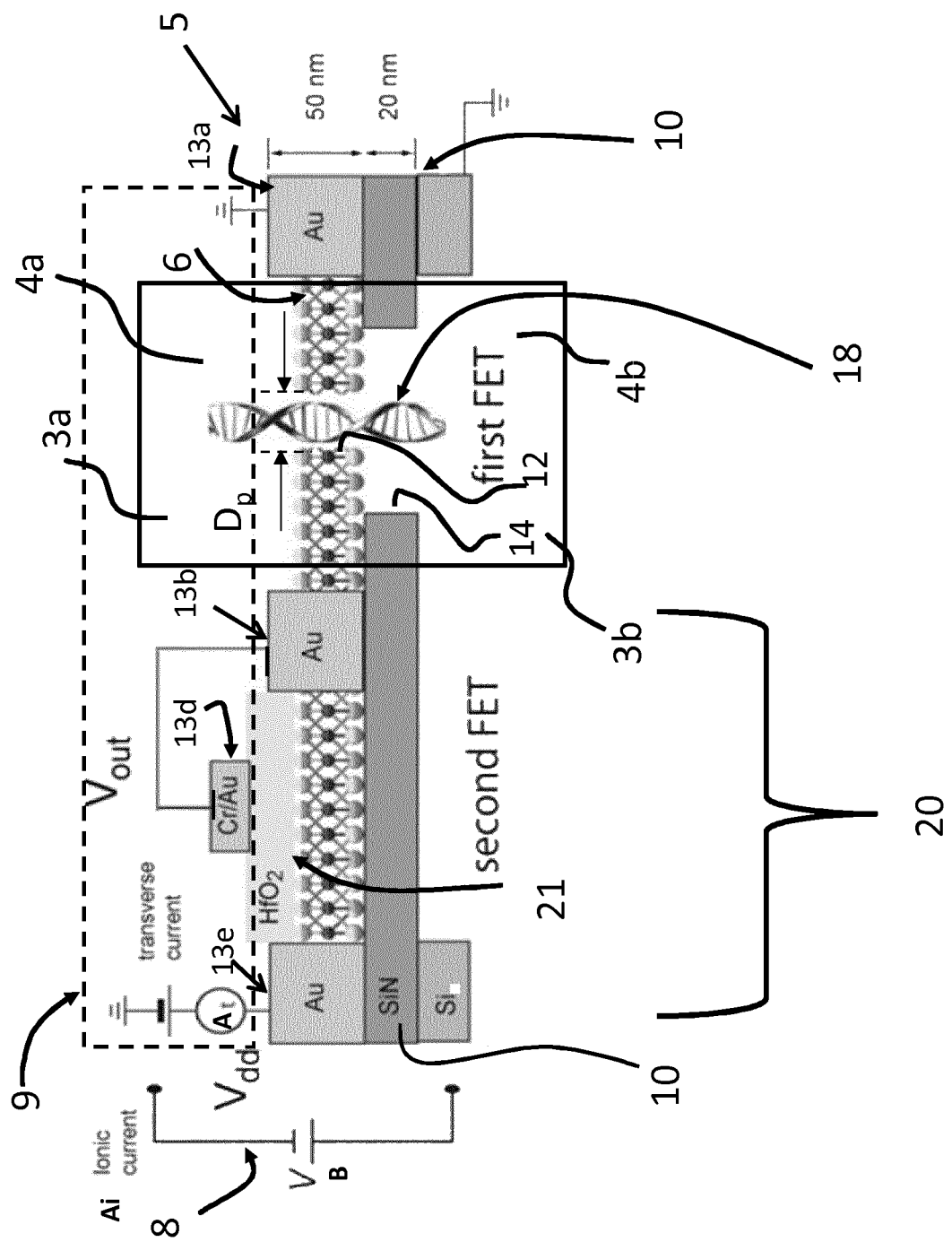

FIG. 13 is an illustration of a molecular sensing system according to an embodiment of the invention in a configuration where the signal of detection of the transverse current change when a biomolecule translocation occurs through the pore(s) is amplified by a small amplifier as described below.

Figure 14:
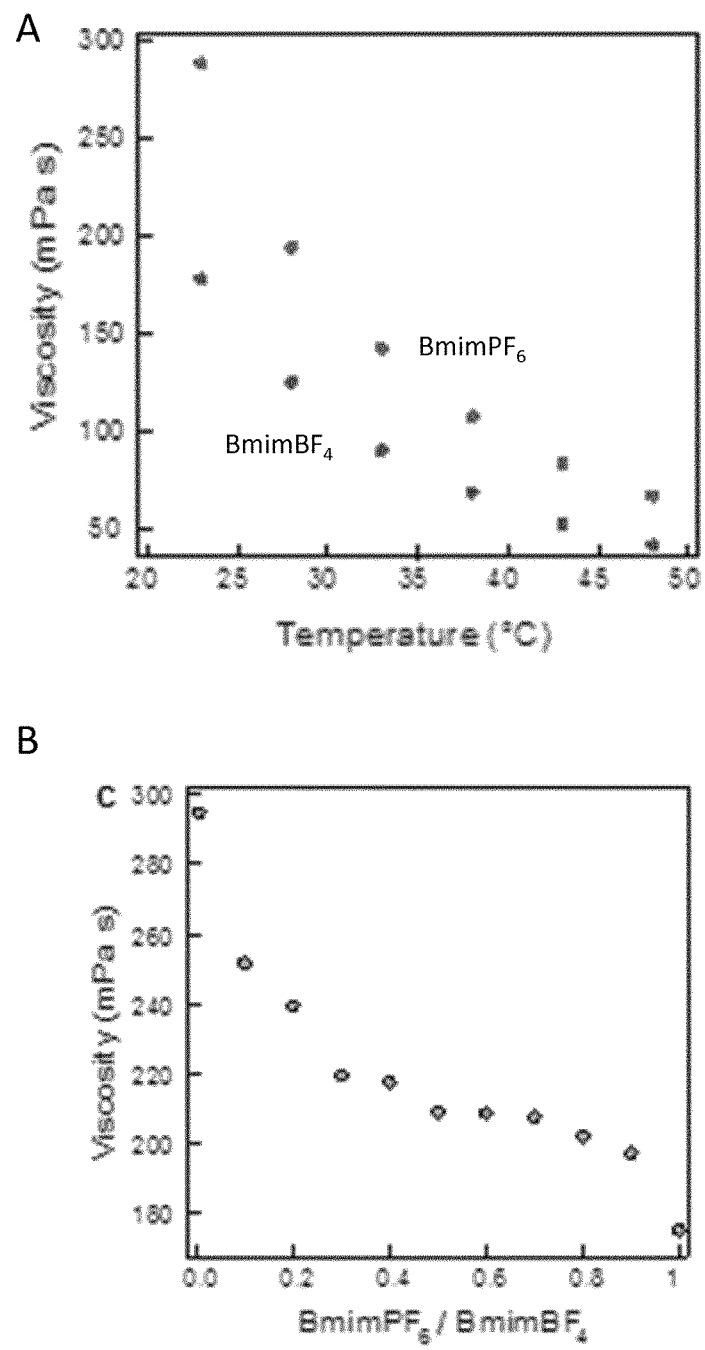

FIG. 14 shows the variation of viscosity of a RTIL of the invention either as a pure RTIL ($Bmim(PF_6)$ or $Bmim(PF_4)$) versus the temperature (A) or as a mixture of $Bmim(PF_6)$ and $Bmim(PF_4)$ as described in Example 5 versus the $Bmim(PF_6)$ to Bmim(PF4) molar ratios at room temperature (data from Khupse et al., 2010, *Bio-Inorganic Physical Theoretical &Analytical Chemistry*, 49, 727) (B).

Figure 15:
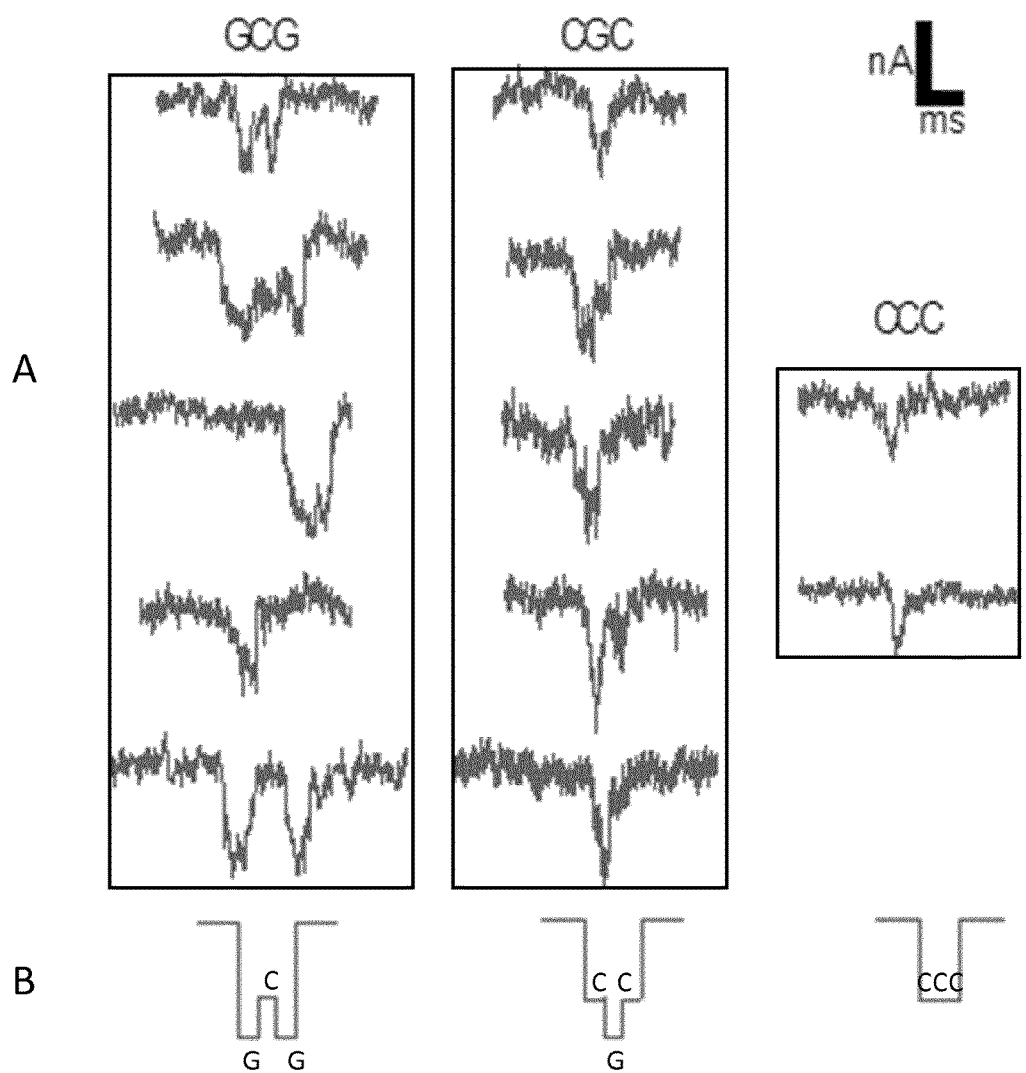

FIG. 15 shows raw homo and hetero-polymer ssDNA translocation events as measured in ionic current variations obtained in single layer $MoS_2$ nanopore sensing device as described in Example 6 for sequences of three-mer nucleotides GCG, CGC and CCC respectively (top). Bottom signals correspond to the ideal shape of the event in the absence of the noise. Obtained shapes and amplitudes of the current drops are in agreement with the current signal drops obtained for single nucleotides as described in Example 4 (bottom) representing first ever re-sequencing in solid state nanopores.

DETAILED DESCRIPTION OF THE INVENTION

Figure 1:
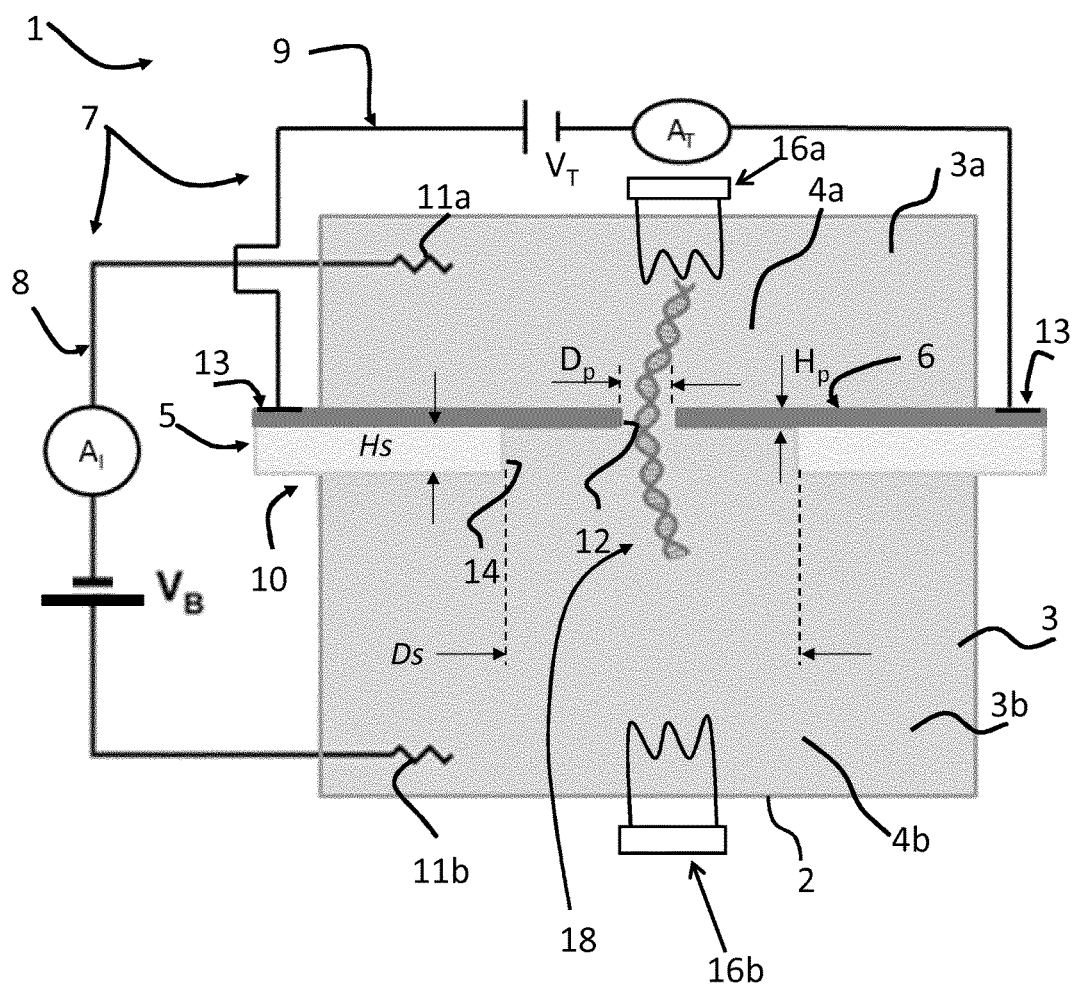
FIG. 1 is a schematic illustration of a molecular sensing system according to an embodiment of the invention.

Referring to the figures, in particular first to FIGS. 1 and 13, a molecular sensing system 1 for sensing a molecular analyte 18 in an electrically conducting liquid 4, comprises a housing 2, a sensing device 5 and a signal processing circuit 7. The housing 2 comprises a first chamber portion 3a containing a first conducting liquid 4a and a second chamber portion 3b containing a second conducting liquid 4b. The sensing device 5 defines the separation between the first chamber portion 3a and a second chamber portion 3b and comprises an active layer 6 and at least one support layer 10 for supporting the active layer in an essentially planar manner. The active layer 6 comprises at least one pore having a pore aperture Dp and a pore height corresponding to the active layer thickness Hp. The support layer 10 comprises a support layer orifice 14 having an aperture diameter Ds and an aperture height corresponding to the support thickness Hs.

The signal processing circuit 7 comprises an ionic current circuit 8 and a transverse current circuit 9. The ionic current circuit 8 forms an electrical circuit between a voltage source $V_B$ and the electrodes 11a and 11b immerged into the first conducting liquid 4a and the second conducting liquid 4b, respectively and is configured to generate the ionic current $I_i$. The ionic current circuit may further comprise a current measurement circuit portion Ai configured to measure the ionic current $I_i$ to obtain a signal representative of the characteristics of the section of molecular analyte passing through the pore in the active layer.

In the embodiment of FIG. 1, the transverse current circuit 9 forms an electrical circuit between a voltage source $V_T$ electrically connected to the active layer 6 through electrical terminals 13 and generates a transverse current $I_T$ through the active layer. The transverse current circuit may further comprise a current measurement circuit portion At configured to measure the transverse current It to obtain a signal representative of the characteristics of the section of molecular analyte passing through the pore in the active layer.

In the embodiment of FIG. 13, the transverse current circuit 9 uses the output of the transverse current as an intermittent gate to apply an input signal on a field effect transistor (FET). A transverse current circuit similar to that found in the embodiment of FIG. 1 is mounted in series with an FET to lead to a small signal amplifier as described in Radisavljevic et al., 2012, *Applied Physics Letters* 101. The local potential change induced by a biomolecule translocation through the pore acts as the small signal input to the amplifier and the output voltage ($V_{out}$) is read on the middle connector of the transistor. The total amplification of the signal is regulated by the power supply voltage $V_{dd}$ of the transistor.

As shown in FIG. 13, the transverse current circuit 9 comprises an electrical circuit formed between a voltage reference such as ground, electrically connected to the active layer 6 through an electrical terminal 13a, and an output terminal 13b connected to a gate 13d of a FET. A transverse current $I_{T1}$ through the active layer thus generates a voltage output from the active layer ($V_{out}$) used as an intermittent gate input (voltage varies while biomolecular analyte 18 translocates) to a transverse current amplifying system 20 of the transverse current circuit 9. The transverse current amplifying system 20 electrically connected to the active layer 6 through electrical terminal 13c and electrical terminal 13d where the electrical terminal 13c is in electrical contact with the active layer 6 and the electrical terminal 13d is in electrical contact with the semi-conducting element 21 from the transverse current amplifying system 20. The transverse current amplifying system 20 comprises a voltage source $V_{dd}$ which regulates amplification of the transverse current voltage output $V_{out}$ to generate an amplified transverse current measured by the transverse current measuring system $A_T$.

It is known per se that the presence of a translocating molecule locally changes potential and modulates a transverse current as demonstrated in Traversi et al., 2013, *Nat. Nanotechnol.*, 8, 939-945.

Concomitant measurements of ionic and transverse currents can be then analyzed by detection software such as the one described in Raillon et al., 2012, *Nanoscale* 4: 4916-4924 which is based on cumulative sum, which allow fast and automated detection of events and their levels even when signal to noise is close to 1.

According to an aspect of the invention, the active layer 6 is made of a semi-conducting material. The semi-conductive material may advantageously comprise or constitute a layered semi-conductive material which can be exfoliated in thin layer(s), in particular atomically-thin layer(s) (e.g. $MoS_2$ $MoSe_2$, $MoTe_2$, $WS_2$, $WSe_2$, $WTe_2$, $TiS_2$, $TiSe_2$, $TiTe_2$, $HfS_2$, $HfSe_2$, $Hfre_2$, $ZrS_2$, $ZrSe_2$, $ZrTe_2$, $NbS_2$, $NbSe_2$, $NbTe_2$, $VS_2$, $VSe_2$, $VTe_2$, $TaS_2$, $TaSe_2$, $TaTe_2$, $TcS_2$, $TcSe_2$, $TcTe_2$, $ReS_2$, $ReSe_2$, $ReTe_2$, $PdS_2$, $PdSe_2$, $PdTe_2$, $PtS_2$, $PtSe_2$ and $PtTe_2$).

According to another aspect of the invention, the semi-conductive material comprises or constitutes a layered semi-conductive material which can be exfoliated in thin layer(s), in particular atomically-thin layer(s) semi-conductive material from transition metal dichalcogenide (TMD) crystals of chemical formula is $MX_2$, where M is a transition metal atom and X is a chalcogen (S, Se, or Te) (e.g. $MoS_2$, $WS_2$, $TeS_2$, $MoSe_2$, $WSe_2$, and $TeSe_2$). According to a particular aspect, this semi-conductive material can be employed in single, double or multilayer form to form an active layer according to the invention as described in WO 2012/093360, wherein a portion of the active layer extends over its support layer in a suspended manner.

According to an advantageous embodiment, the active layer comprises $MoS_2$ thin layers or is a $MoS_2$ monolayer.

According to an advantageous embodiment, the active layer comprises CVD grown $MoS_2$ thin layers or is a CVD grown $MoS_2$ monolayer.

In an aspect of the invention, the provision of a freestanding suspended portion of semiconductor active layer through which the nano pore is formed allows to benefit from the advantage of being able to apply a transverse current in the active layer and measure the signal affected by the translocation of the molecular analyte, as well as being able to form an accurate nano pore in a very thin active layer without having to drill through a relatively thick support layer because of the suspended freestanding portion of active layer.

Thin layers of $MoS_2$ with good quality suitable for use in a device according to the invention can be prepared by both exfoliation and chemical vapor deposition (CVD) (Novoselov et al., PNAS, 2005, 102, 10541-1053; Liu et al. 2012, Nano Lett., 12, 1538-1544).

According to one aspect, the quality of thin layers of semi-conducting material suitable for use in a device according to the invention can be assessed by photoluminescence, in particular line-width such as described in Dumcenco et al. http://arxiv.org/abs/1405.0129. The excitation energy and intensity will be chosen to probe different regions of the semi-conducting monolayer under various electrostatic and ionic liquid gating conditions and photoluminescence and/or Raman spectroscopy will allow probing the material quality of the active layer. For example, when the excitation laser is set to 680 nm and the beam applied to a single layer $MoS_2$, a strong signal arises due to the fact that single layer $MoS_2$ has direct bandgap and the center of the $MoS_2$ flake exhibits more pronounced photoluminescence than its edge. Photoluminescence mapping of the flakes can be obtained while raster scanning the sample under microscope objective (e.g. with a step wise of 250 nm). These measurements might also be used to determine the degree of electron beam damage during pore drilling. Typically, the thickness of an active layer according to the invention can be assessed by Raman/optical electron microscopy, photo-luminescence (PL) measurements and Atomic Force Microscopy (AFM).

According to another aspect, the active layer is from about 0.3 nm to about 1 nm thick.

According to another particular aspect, the thickness of the active layer is less than 2 nm, typically from about 0.7 nm to less than 2 nm. In particular, the active layer is from about 0.7 nm (e.g. one layer) to about 1.4 nm thick (e.g. two layers).

According to another aspect, pores in the active layer are nanometer sized, typically from about 1 nm to 20 nm diameter (for example typically from about 1 nm to about 5 nm, for example less than 4 nm or less such as about 3 nm) and from about 0.3 nm to 1 nm thickness (for example about 0.7 nm). According to another aspect, the pores are drilled into the active layer with a highly focused electron beam (e.g. in a transmission electron microscope). Typically, the size of the pores can be measured by Transmission electron microscopy (TEM) and calculated from the current voltage characteristics.

According to another aspect, the support layer can be a $SiN_x$ glass, or quartz (or any other material that provides low capacitance membrane) with a support orifice according to the invention. According to a further aspect, the support orifice has typically a diameter of from about 20 nm to about 500 nm (e.g. 50 nm), like for example from about 200 nm to about 500 nm and from about 20 nm to 50 nm thick.

According to a further aspect, the support layer can be coated with some curing layer such as polydimethylsiloxane (PDMS), while leaving the $MoS_2$ nanopore exposed in order to reduce the dielectric noise. Alternatively, support layer can be a quartz, glass, or any other material that provides low capacitance membrane based support.

According to another aspect, a viscosity gradient is created between the first electrically conducting liquid in the first chamber portion (cis chamber) and the second electrically conducting liquid in the second chamber portion (trans chamber). In particular, according to a further aspect, the first electrically conducting liquid is a "room temperature ionic liquid" (also known as "RTIL") and the second electrically conducting liquid is an aqueous ionic solution (e.g. water and KCl or any inorganic salts such as LiCl, NaCl, $MgCl_2$ $CaCl_2$ etc.). "Ionic liquids" are non-aqueous electrolytes only composed of loosely coordinated bulky ions forming pairs of organic cations and anions and have been largely described (Chiappe et al., 2005, J. Phys. Org. Chem, 18: 275-297; Keskin et al., 2007, J. of Supercritical Fluids, 43, 150-180; Carda-Broch, 2003, Anal. Bioanal. Chem., 375: 191-199).

According to a further aspect, RTILs according to the invention have a viscosity at room temperature not less than about 100 cP. According to a further aspect, RTILs according to the invention have a viscosity at room temperature from about 100 cP to about 10,000 cP, in particular from about 100 cP to about 500 cP and more particularly from about 100 cP to about 300 cP, tuneable in a wide range upon RTILs chemical composition. According to a further aspect, RTILs according to the invention may be selected from the following group based on the anion nature: (a) systems based on $AlCl_3$ and organic salts such as 1-butyl-3-methyl-imidazolium chloride, [bmim][Cl]; (b) systems based on anions like $[PF_6]^-$, $[BF_4]^-$ and $[SbF_6]^-$; (c) systems based on anions such as $[CF_3SO_3]^-$, $[(CF_3SO_2)_2N]^- \equiv [Tf_2N]^-$ and similar; (d) systems based on anions such as alkylsulfates and alkylsulfonates; (e) carboranes ($[CB_{11}H_{12}]^-$, $[CB_{11}H_6Cl_6]^-$, $[CB_{11}H_6Br_6]^-$) and orthoborates.

According to a particular embodiment, a RTIL according to the invention comprises hexafluorophosphate anions.

According to a further aspect, RTILs according to the invention may include N,N-dialkylimidazolium cations such as dibutyl, dioctyl, dinonyl, didecylimidazolium, 1-Butyl-3-methyl and 1-ethyl-3-methylimidazolium cations ($[bmim]^+$ and $[emim]^+$) According to a particular embodiment, a RTIL according to the invention comprises 1-Butyl-3-methyl and 1-ethyl-3-methylimidazolium cations.

According to a particular embodiment, a RTIL according to the invention comprises tetrafluoroborate anions. According to a further aspect, a RTIL according to the invention is 1-butyl-pyridinium tetrafluoroborate ($BPBF_4$).

According to another particular embodiment, a RTIL according to the invention is selected from the following group: 1-butyl-3-methylimidazolium hexafluorophosphate ($BmimPF_6$), 1-butyl-3-methyl imidazolium tetrafluoroborate ($BmimBF_4$), 1-butyl-3-methyl-imidazolium chloride (BmimCl), and 1-butylpyridinium tetrafluoroborate ($BPBF_4$) or a mixture thereof.

According to another particular embodiment, a RTIL according to the invention comprises nitrate ions. According to a further aspects, a RTIL according to the invention is [C$_4$mim][NO$_3^-$] where C4mim is 1-n-butyl-3-methylimidazo Hum.

According to another particular embodiment, a RTIL according to the invention is 1-butyl-3-methyl-imidazolium chloride (BmimCl).

According to a further aspect, a RTIL according to the invention is 1-butyl-3-methylimidazolium hexafluorophosphate (BminPF$_6$). According to one aspect, BmimPF$_6$ has the advantage of presenting a broad viscosity window of 10-400 cP which is tunable according to needs by changing chemical composition of RTILs and it is a friendly solvent for bio-molecules, while, most importantly, it exhibits good ionic conductivity 1.4 mS cm$^{-1}$. In contrast, low conductivity of glycerol limited previous attempts to narrow viscosity window (1.2-5 cP) and consequently achieved only modest improvement in DNA translocation time 3 base/µs.

According to a particular embodiment, a first conducting liquid comprising a RTIL according to the invention comprises an essentially pure RTIL, or a RTIL mixed with at least one organic solvent (typically ethanenitrile, 2-propenenitrile, methanol, dichloromethane, 1,2-dimethoxyethane, toluene, 1,4-dimethylbenzene or dimethyl sulfoxide (DMSO)), such that the RTIL or its mixture with said optional organic solvent results in a solution having a viscosity (cP1) at room temperature from about 100 centipoises (cP) to about 500 centipoises (cP), in particular from about 100 cP to about 300 cP.

According to a particular embodiment, a first conducting liquid comprising a RTIL according to the invention comprises a water-miscible room temperature ionic liquid (RTIL) mixed with water whereby the water content from about 5 to about 70 wt %, in particular less than 50 wt % resulting in a solution having a viscosity (cP1) at room temperature from about 100 centipoises (cP) to about 500 centipoises (cP), in particular from about 100 cP to about 300 cP.

According to another particular embodiment, a first conducting liquid comprising a RTIL according to the invention is a water-miscible room temperature ionic liquid (RTIL) mixed with water whereby the water content is less than 50 wt %.

According to a particular embodiment, a RTIL according to the invention is selected from [C2mim][BF$_4$], where C2mim stands for 1-ethyl-3-methylimidazolium, [C4mim][BF$_4$], [C4mim][NO$_3$] and [Bmim][PF$_4$]. In the absence of water, their viscosity ranges from (70-300 mPa s, i.e. cPo) and as they are water miscible, the viscosity of first conducting liquid can be tuned for use according the invention by adjusting water content that can range from (5-70 wt %) as described in Seddon et al., 2000, *Pure Appl. Chem.*, 72, 2275. According to one aspect, viscosity of [C4mim][BF4] can be increased with the addition of the chloride ions from 200-1'800 mPa s by adjusting the molar content of Cl in the range from (0-2 mol/kg).

According to another particular embodiment, a RTIL according to the invention is a mixture of BmimPF$_6$ and BmimBF$_4$.

According to one aspect, a first conducting liquid comprising a RTIL according to the invention is a mixture of BmimPF$_6$ and BmimBF$_4$ in a mass ratio varying from 0 to 1 wherein such mixture has a room temperature viscosity spanning over a wide viscosity range of 300-180 mPa·s (Khupse et al., 2010, *Indian Journal of Chemistry Section a-Inorganic Bio-Inorganic Physical Theoretical & Analytical Chemistry* 49: 727-730), allowing to vary the probe retardation component that originates from Stokes drag (FIG. 14).

According to a particular aspect, the viscosity of a RTIL of the invention can be adjusted through temperature control. According a further particular aspect, a RTIL used according to the invention is a mixture of BmimPF$_6$ and BmimBF$_4$ mixed in a mass ratio over a range from 0 to 1, at a temperature between about 20° C. to about 40° C. such that those mixtures have viscosity spanning over a wide viscosity range from about 100 to about 300 mPa·s. Examples of viscosity modulation of RTIL mixture of the invention are provided in the Examples.

According to another embodiment, the viscosity of the RTIL can be fine-tuned either by temperature change which should impact the DNA translocation speed, allowing tailoring DNA translocation speed according to the detection needs.

According to a particular embodiment, the first chamber portion 3a comprises a temperature regulation system 16a in order to control temperature of the first conducting liquid 4a. According to a further embodiment, the temperature regulation system comprises a temperature sensing element and a heating/cooling member.

According to a further particular embodiment, the temperature element system 16a comprises a Peltier element.

According to a further particular embodiment, it is advantageous to provide a sensing chamber comprising a temperature regulation system such that the sensing chamber temperature is regulated (typically at a temperature between about 4 and 60° C.), not only for maintaining the viscosity of the first conducting liquid in the desired range, but also for decreasing the noise caused by the ions due to thermal fluctuations.

According to one embodiment, the temperature regulation system comprises a first temperature regulating system 16a for controlling temperature of the first conducting liquid 4a and a second temperature regulating system 16b for controlling temperature of the first conducting liquid 4b.

According to another aspect, is provided a temperature regulation system controlling both temperatures of the first conducting liquid 4a and of the first conducting liquid 4b.

According to a particular embodiment, the second chamber portion 3b comprises a temperature regulation system 16b in order to control temperature of the second conducting liquid 4b. According to a further embodiment, the temperature regulation system comprises a temperature sensing element and a heating/cooling member.

According to another embodiment, the DNA translocation speed can be further controlled through modulation of pore surface charge change, for example through light illumination (e.g. under visible laser illumination as described in Di Fiori et al., 2013, *Nature Nanotechnology*, 8: 946-951) or through local gate modulation as described in He et al., 2011, *ACS nano*, 5: 5509-5518 in order to enable discrimination between individual nucleotides when present in a typical sample.

According to an embodiment is provided an example of a device according to the invention as schematized in FIG. 2a, where few layers or even monolayer MoS$_2$ (active layer) are suspended on the pre-etched square-shaped opening on the 20 nm thick supporting SiN$_x$ membranes (support layers). In this configuration, the analyte (e.g. DNA) can translocate through subnanometer thick MoS$_2$ active layer instead of 20 nm thick SiN$_x$ to achieve a better spatial resolution. A transfer method (Petrone et al., 2012, *Nano Lett.*, 12, 2751-2756) was used to suspend monolayer and few-layer MoS$_2$ on SiNx supporting layers and high resolution electron to microscopy technique was used to sculpt nanopores in variable diameters on the in free-standing MoS$_2$ active layers. Pore forming example is provided in the Example section below. Micromechanical exfoliation method (Nanoselov, 2004, *Science*, 306, 666-669) was used to exfoliate few-layer MoS$_2$ from natural MoS$_2$ bulky material onto the surface of substrates covered with 270 nm SiO$_2$ chips with fiducial markers. An optical microscope is used to identify single and few layers MoS$_2$ by their contrast under illumination.

As shown in FIG. 2b, monolayer MoS$_2$ shows minimum contrast with respect to the substrate. The coordinates of chosen flakes were recorded and used for the further transfer onto the SiN$_x$ support layer. To verify the thickness of this chosen flake, atomic force microscopy (AFM) was used to obtain its height profile, as shown in FIG. 2d. The thickness is 9 Å from AFM measurements and is indicative of a monolayer, which is consistent with the optical observation. Subsequently, this flake was transferred from the silicon dioxide substrate to a square-shaped opening (ranging from 200 to 500 nm in size to reduce electric noise when flake in contact with ionic buffer) on the target SiN$_x$ supporting layer using a standard graphene transfer method (Petrone et al., 2012, *Nano Lett.*, 12, 2751-2756). FIG. 2c is the optical image after a successful transfer of the flake shown in FIG. 2b,d to the desired location (marked by the black circle) on the support layer. TEM with low magnification was used to search for the chosen flake. FIG. 2e illustrates the full coverage of the opening in SiN$_x$ by the flake (marked by the black circle), preventing ionic current leakage. The MoS$_2$ lattice can be clearly resolved in the high-magnification image with the diffraction pattern (DP) reflecting the hexagonal symmetry of MoS$_2$. The drilling process of the pore lasts only for several seconds after which a nanometer-sized pore appears within the MoS$_2$ layer. This is another indication that the pore was drilled through only few atoms of MoS$_2$. Therefore, a good thermal and mechanical stability is highly preferred for such a short drilling period, especially in the case of small pores. The beam is preferably blanked for several minutes before the drilling process starts in order to minimize the drift for the both beam and the active layer sample. FIG. 2f-i shows several examples of nanopores with various sizes.

Figure 3:
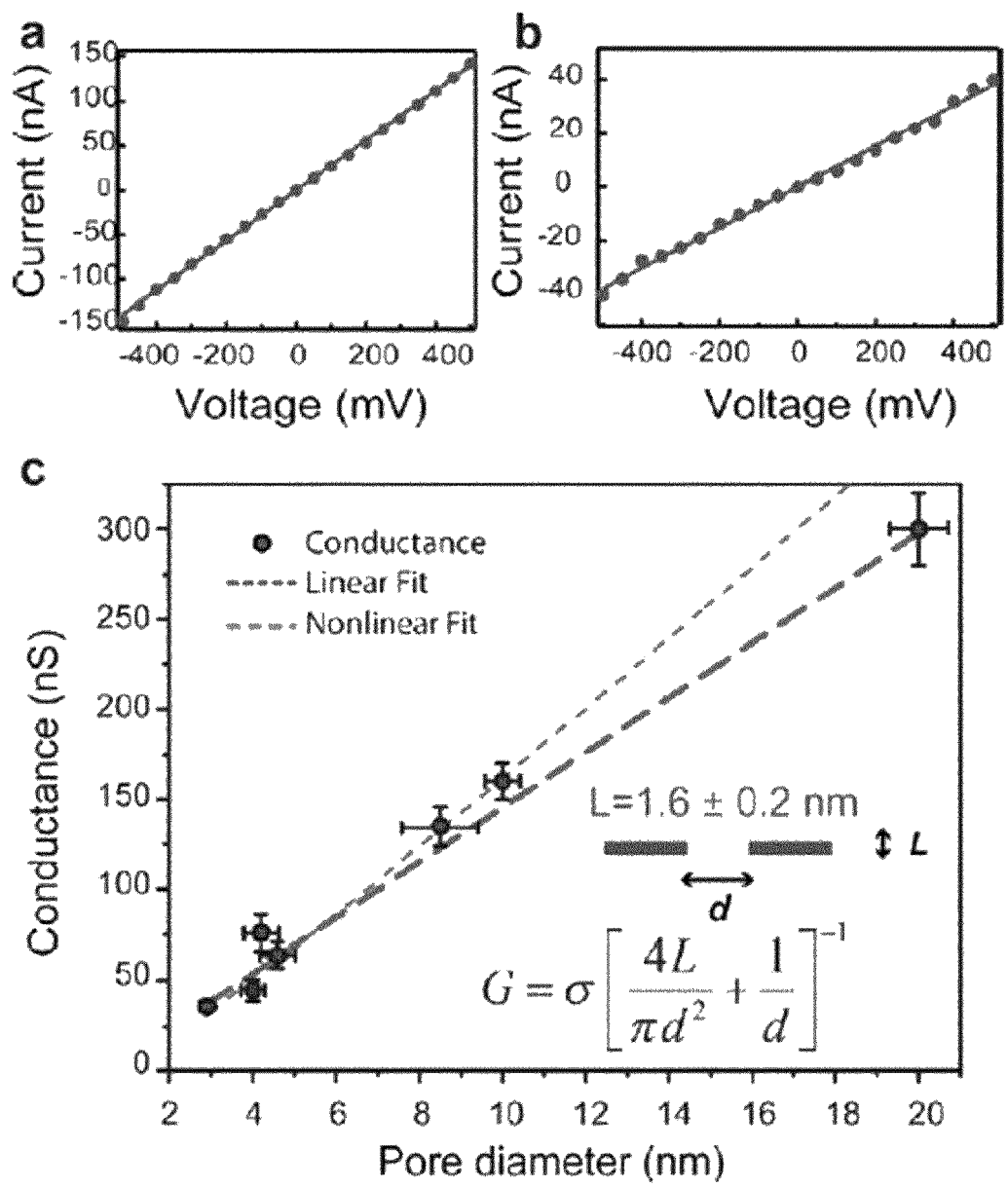
FIG. 3 shows the characterization of a nanopore according to the invention described in Example 1. a) Current voltage characteristic of a 20 nm $MoS_2$ nanopore measured in 2 M KCl; b) Current voltage characteristics of a 5 nm $MoS_2$ nanopore measured in 2M KCl; c) Correlation between pore diameters and their conductances. Conductances are derived from linear fits of IV measurements in 2 M KCl with bias voltage swept from −0.5 to +0.5 V. To exclude either leaking pores G>300 nS or clogged pores G<10 nS, only devices displaying conductances higher than 10 nS and lower than 300 nS were used. Error bars of the pore diameters indicate the asymmetry of the pores. Inset shows a simple scheme for the thin active layer with a nanopore and related equation to describe conductance, where G is conductance, 6 is ionic conductivity, L is thickness and d is pore diameter. The nonlinear fitting (small dot line) is based on the equation 1 shown in the inset to subtract L. And the linear fitting (large dot line) is based on the simplified equation 2, G=σd, to subtract 6.

Moreover, in some cases the number of layers can be identified by inspecting the folded edges of the flake. The current-voltage (IV) characteristics of MoS$_2$ nanopores with various sizes (2-20 nm) was investigated when immersed in the 2 M KCl buffered solution as electrically conducting liquid. FIG. 3 a,b shows examples of IV curves measured in the KCl buffer, exhibiting linear and symmetric characteristics from 500 to 500 mV. According to the model first proposed by Wanunu et al., 2010, *Nat. Nanotechnol.*, 5, 807-814 and later Kowalcyzk et al., 2011, *Nanotechnology*, 22, 315101 the conductance of nanopore can be described by equation 1:

$$G = \sigma \left[ \frac{4L}{\pi d^2} + \frac{1}{d} \right]^{-1} \quad (1)$$

where σ, L and d are the ionic conductivity of 2 M KCl (20 S m$^{-1}$), membrane thickness and nanopore diameter, respectively. Two major elements associated with pore geometry contribute to the conductance, namely channel resistance (the first term in the equation) and access resistance (the second term in the equation). FIG. 3c shows a plot of all working devices in this study. Using a nonlinear fit, L was obtained with a value of 1.6 (0.2 nm, reflecting an atomically thin feature of the MoS$_2$ active layers. For an ultrathin membrane, channel resistance is much smaller than the access resistance. Therefore, the conductance can also be expressed as equation 2:

$$G = \sigma d \quad (2)$$

As a result, a nearly linear relationship between pore conductance and pore diameter is expected. From a linear fitting, σ was found with a value of 17.5±1.5 S m$^{-1}$, which is in a good agreement with ionic conductivity of 2 M KCl (20 S m$^{-1}$). Therefore, both fits are suitable. At any given pore size, the conductance from MoS$_2$ nanopore is much larger than that of SiN$_x$. Moreover, no influence of the number of layers (always less than 4) was observed on the conductance since the pore diameter is larger than its thickness.

Figure 4:
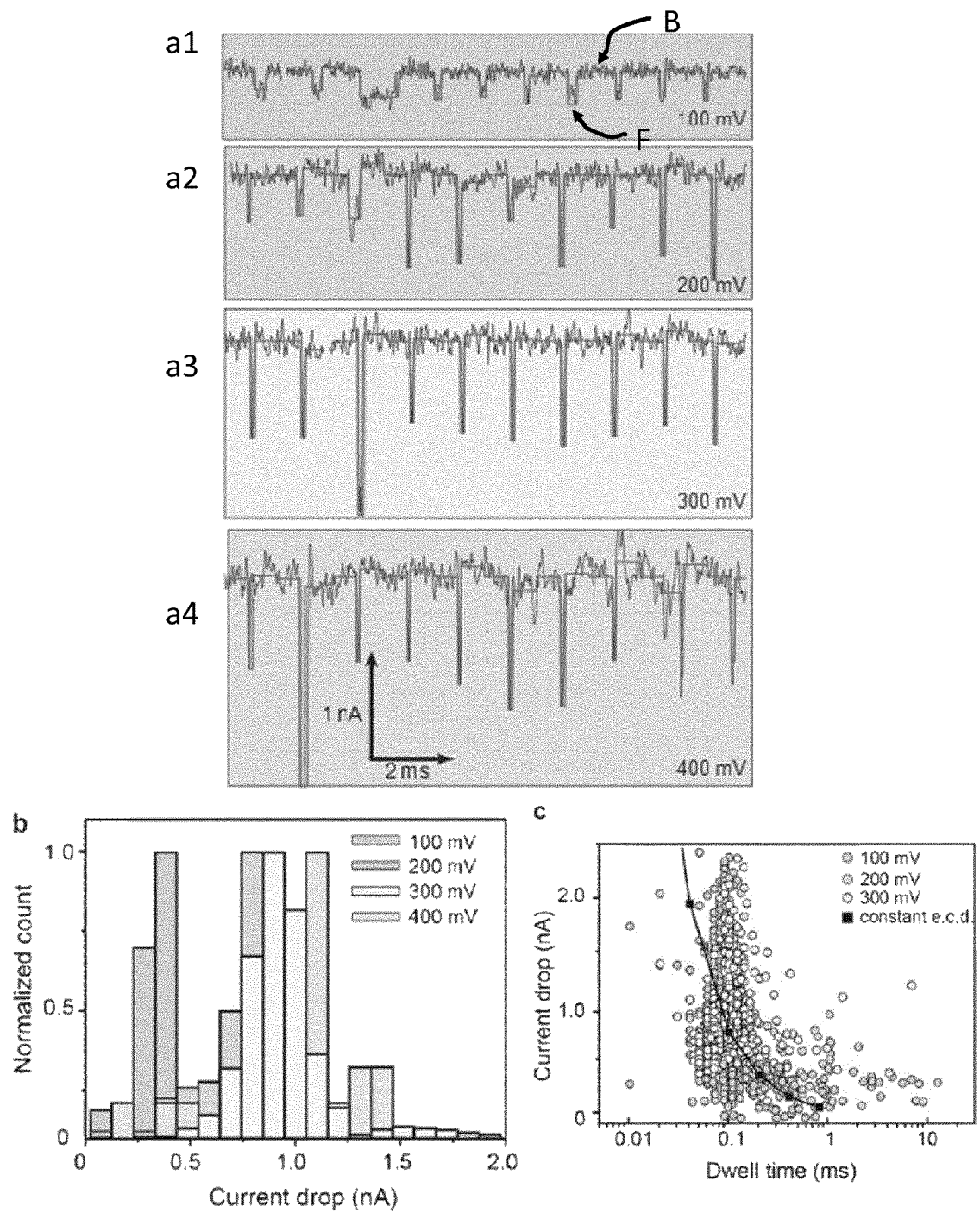
FIG. 4 shows signal analysis as conducted under Example 1. a1-a4) Concatenated events of pNEB plasmid DNA translocating a 20 nm $MoS_2$ nanopore in 2MKCl. Raw signal (B) and fits (F). Fits are performed using a custom "Open-Nanopore" Matlab code; b) Normalized distribution of current amplitude at various voltages; c) Scatter plots of 59, 1823, and 1642 events for 100, 200, and 300 mV, respectively. An electron charge deficit (ECD) method is used to fit the area of individual events.

Ideally, (K$^+$, Cl$^-$) ions flow in two directions under the influence of the electrical field (ionic current circuit) through a nanopore resulting in a constant ionic current, namely, the baseline current. DNA translocation will give rise to temporary blockades in ionic pore current manifested by a decrease in ionic current on the time-scale of approximately 100 μs to 10 ms, as shown in FIG. 4a. pNEB plasmid DNA was first translocated through a 20 nm diameter MoS$_2$ nanopore to eliminate the multiple conformation issue. Two parameters, the amplitude of blockage and dwell time are used to quantify individual translocation events. Cumulative sums (CUSUM) algorithm was used to detect events automatically and extract above-mentioned parameters for each event (Raillon et al., 2012, *Nanoscale*, 4, 4916-4924). Events are concatenated with short segments of the baseline signal preceding and following them. Due to the circular shape of the pNEB plasmid, all events have only one level indicating a single conformation. The signal amplitude also increases upon raising the applied voltage as shown in FIG. 4b. Mean signal amplitudes are 0.3, 0.7, 0.9, and 1.1 nA for 100, 200, 300, and 400 mV, respectively. The ratio 2*(2.2/d)$^2$ was used to calculate theoretical blockage, where d=20 nm in this case. Blockage percentage is 2.4%, in accordance with the experimental value of 1.5%. Scatter plots are used to describe the statistics of DNA translocation as shown in FIG. 4c. For voltages above 200 mV, fast translocation is observed with a most probable dwell time of <100 μs. But for 100 mV, a much broader distribution (200 μs full-width at half-maximum) is observed with a mean dwell time of <300 μs.

A constant electron charge deficit (ECD) to fit the scatter plot (FIG. 4c) for various Voltages was used. As a result, a value of <500 ke is obtained, which is at least five times of previously reported data for 3 kbp DNA (Fologea et al., 2005, supra). This increase is mainly due to the increased blockage amplitude because of the greatly improved sensitivity of MoS$_2$ nanopores compared to conventional SiN$_x$ nanopores (current drop here found of <400 pA at 100 mV as compared to <100 pA at 100 mV, earlier reported).

It is very advantageous to have a good signal-to-noise ratio (SNR), preferably more than 6, for event detection. In this configuration SNR was >10 (100 pA RMS noise and <nA signal). The percentage of device failure (conductance higher than 300 nS due to leakage or lower than 10 nS due to pore clogging) in solution is surprisingly low (<30%).

When pNEB DNA was translocated through a 5 nm diameter MoS$_2$ pore according to this configuration under the same experimental conditions (representative concatenated traces observed), both mean current amplitude and mean dwell time are larger for the 5 nm pore compared to the 20 nm pore as observed on a scatter plot, implying a local interaction between the edge of the MoS$_2$ pore and the DNA molecule. To extend this statement, this interaction happens only when DNA is sliding through the edge of pore with the effect of retarding DNA translocation. For larger pores (20 nm), translocations tend to be in a frictionless manner.

The present example of a device of the invention shows that the active layers with a single size-tunable nanopore can be produced with good yield and very low device failure rate when working in high ionic strength buffers and that translocation of various types of DNA trough MoS$_2$ pores exhibits a signal amplitude that is five times higher than in the case of solid-state Si$_3$N$_4$ active layers and a SNR of more than 10. These features are highly desirable for event detection which were used to show the electric-field induced unfolding of a 48 kbp long DNA molecule within the nanopore which manifests itself in the quantization of the current drop.

Therefore, semi-conducting active layers, such as MoS$_2$ nanopore active layers can compete with graphene nanopore active layers in terms of spatial resolution and possibly better performance for transverse detection of analyte translocation.

Figure 5:
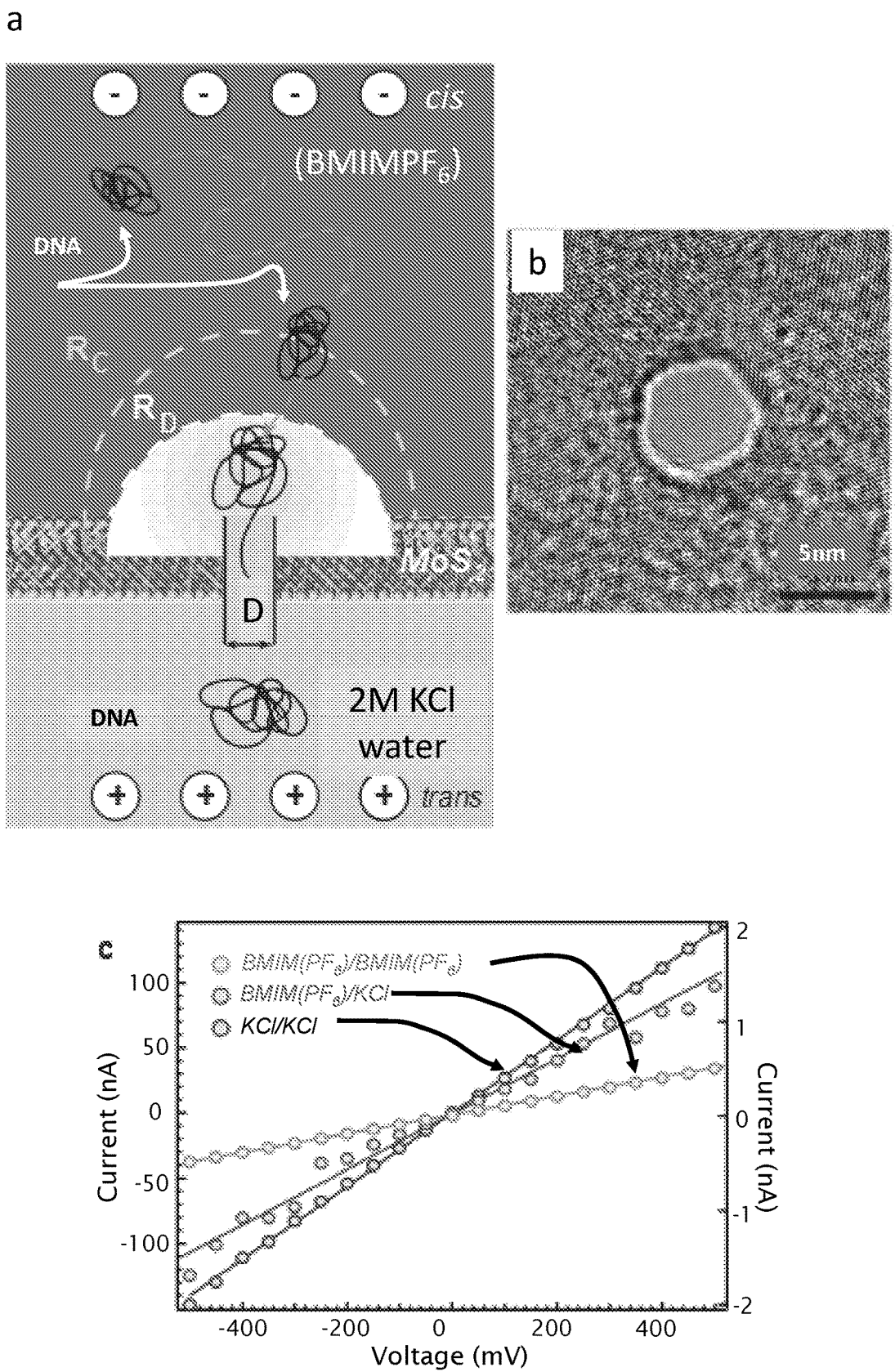
FIG. 5 is schematic and characterization of the RTILs/KCl viscosity gradient system in 2d material nanopore as described in Example 3; a) Cis chamber contains RTILs ($BmimPF_6$) while trans chamber contains 2M aqueous KCl solution. The two chambers are separated by monolayer $MoS_2$ as active layer with a nanopore. Dynamics of DNA translocation through a monolayer $MoS_2$ nanopore is also displayed. Away from the pore, DNA motion is purely diffusive due to the negligible electric field, but once within the area of capture radius Rc, DNA will be accelerated towards the pore by the force due to electrophoretic and electroosmotic effects, next a part of DNA will undergo conformation change and one end will dive into the pore. The non-translocated part of the DNA polymer-monomers will keep the coil conformation and experience a strong Stokes dragging force from the ionic liquids. Consequently, DNA translocation through the pore can be significantly slowed down; b) Bright-field TEM image of a 5-nm solid-state pore fabricated in a monolayer $MoS_2$ as active layer suspended over a 200 nm×200 nm etched area formed in the center of 20 μm big low-stress SiN membrane being 20 nm thick; c) Ohmic current-voltage responses for the $MoS_2$ pore shown in b). IV characteristics are taken at room temperature 2M aqueous KCl solution, in pure $BmimPF_6$ and finally in $BmimPF_6$/2M KCl gradient; d) Mass fraction of water, anions ($PF_6^-$ and $Cl^-$, cations ($Bmim^+$ and $K^+$) as a function of distance from the nanopore; e) Electric potential map evaluated numerically for viscosity gradient system shown in a).
Figure 5:
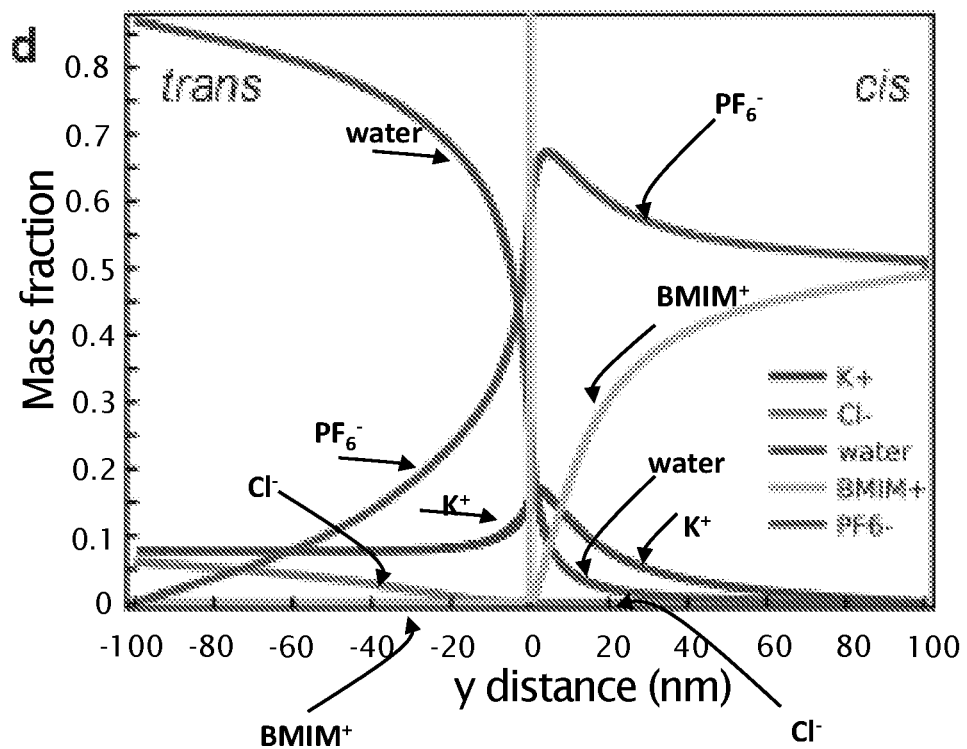
Figure 5:
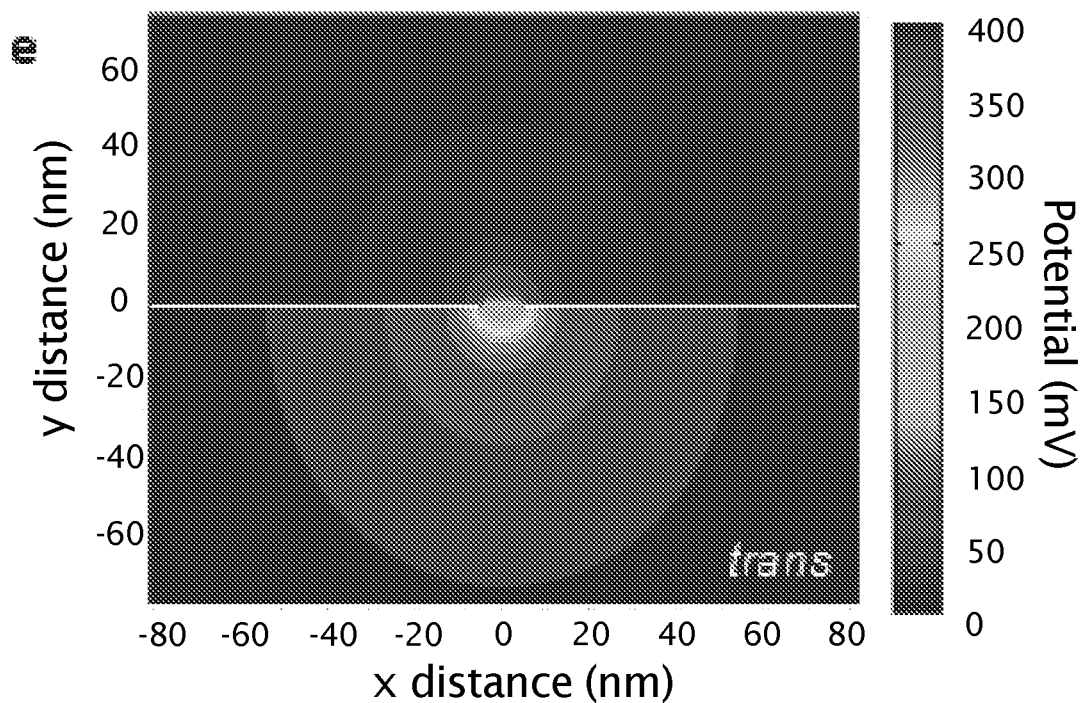
Figure 6:
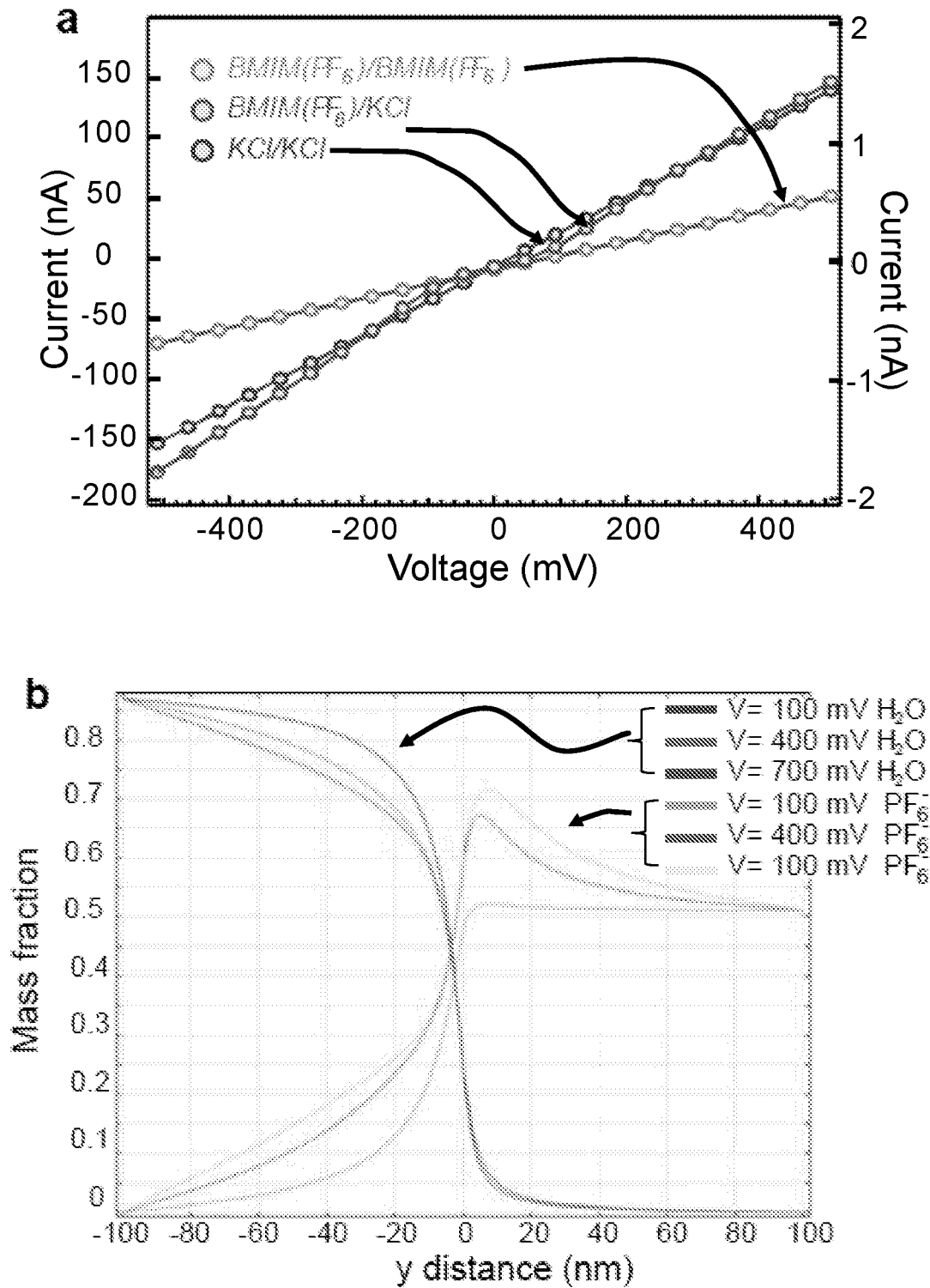
FIG. 6 shows modeling results of the RTILs/KCl viscosity gradient system in 2d material nanopore as described in Example 3; a) COMOSOL modeling of the conductance for the $MoS_2$ pore; b) COMOSOL modeling of the mass fraction of specimen in the vicinity of the MoS2 nanopore.
Figure 7:
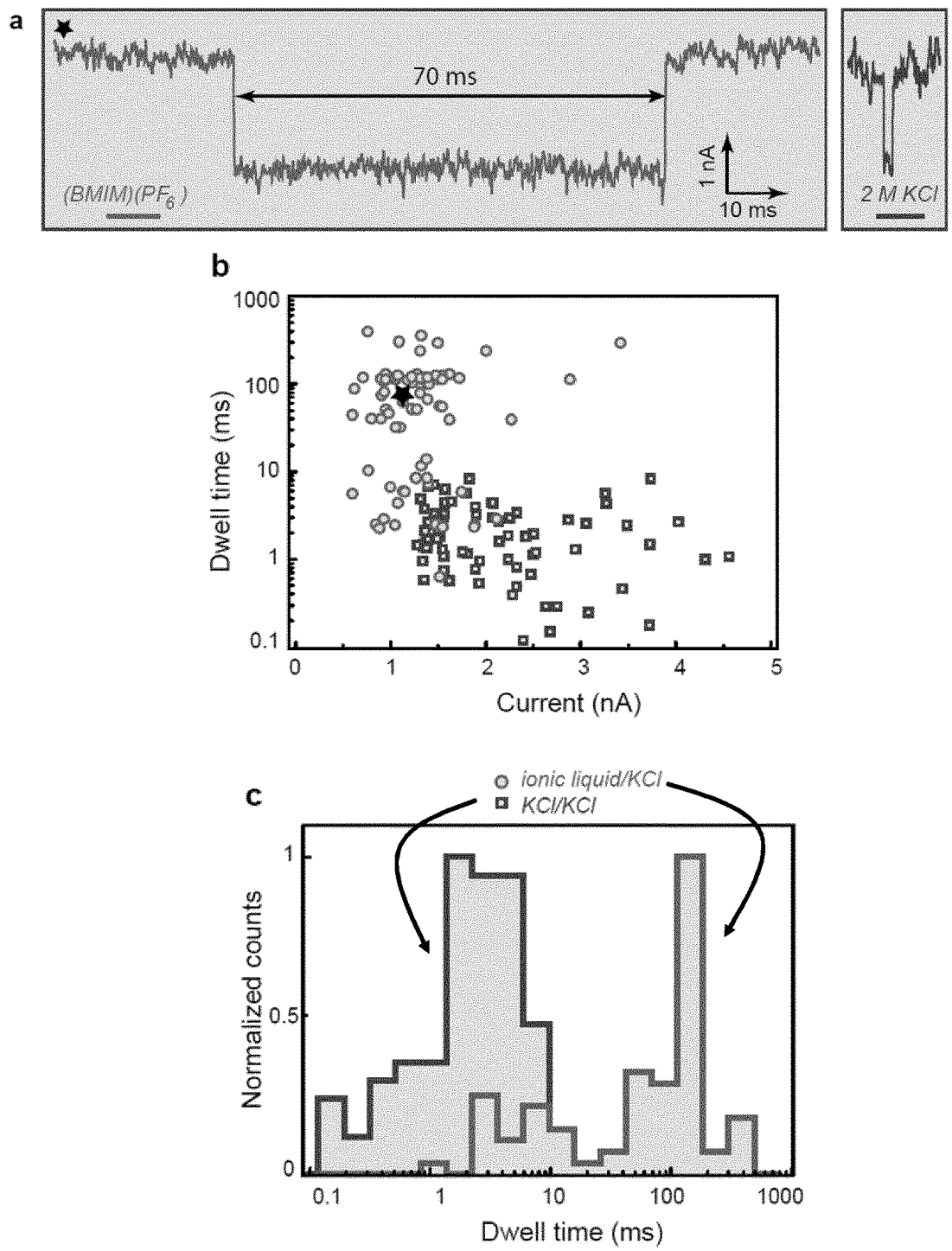
FIG. 7 shows the slowing down DNA translocation by increasing the electroosmotic Stokes force FS in monolayer $MoS_2$ nanopore in a device of Example 3; a) An example of 48.5 kbp λ-dsDNA translocation event in viscosity gradient system (left). The corresponding current drop represents a single DNA molecule passing through the pore. When compared to the typical translocation trace for 48.5 kbp λ-dsDNA obtained using a same 20 $MoS_2$ nanopore under no viscosity gradient conditions, DNA the 2 order of magnitude difference in translocation time is evident (right); b) Scatter plots (blockade current versus dwell time) for dwell time versus current signal of λ-dsDNA translocation in water (squares) and viscosity gradient system (dots) obtained using a same 20 nm big $MoS_2$ nanopore; c) translocation time histograms corresponding to λ-dsDNA translocation in water (left), viscosity gradient system (right).

According to another embodiment is provided an example of a device according to the invention as schematized in FIG. 5a where a 5 nm MoS$_2$ nanopore is used in combination with a viscosity gradient between the first conducting liquid and the second conducting liquid, the first conducting liquid being pure BmimPF$_6$ where a conductivity of 200 nS was achieved. (FIG. 5d). FIG. 5d shows mass fraction of water molecules, anions and cations as a function of distance from the nanopore at 400 mV transmembrane bias (V$_B$). Sub-nanometer membrane thickness ensured that via diffusion process relatively high number of water molecules diffused from trans (second chamber portion) into cis chamber (first chamber portion), similarly, anions and cation molecules diffused into respective chamber. Modeled conductances shown in FIG. 6a are in good agreement with the measurements. Interestingly, mass fraction of water molecules in cis chamber weakly depends on transmembrane bias, while PF$_6$ anions diffusion is strongly affected FIG. 6b. Therefore, this set-up proved that it was possible to employ pure BmimPF$_6$ without compromising the conductance of the MoS$_2$ nanopore. This supports that a well-characterized viscosity gradient system has been built. Translocation of a 48.5 kbp λ-dsDNA was achieved by adding the plasmid into the cis chamber filled with pure BmimPF$_6$. In order to minimize nanopore-DNA interaction that can also significantly contribute to the DNA translocation retardation, slightly bigger MoS$_2$ nanopores (~20 nm) were used. FIG. 7a displays the typical current trace of translocating lambda DNA molecule in viscosity gradient system at 400 mV, if compared to the typical current trace in 2M aqueous KCl solution obtained using a same pore and applying the same voltage, one can observe temporal improvement and no reduction in the current amplitude drop. The amplitudes of ionic current blockage and the translocation times, are extracted using custom Matlab routines. The average translocation time is 130 ms for lambda DNA in ionic liquids, while 1.4 ms in KCl solution. At this point, for the same pore, same DNA molecule and the same biasing electric field, a retardation factor can be introduced and can be defined as equation 3:

$$r = \frac{v_{H_2O}}{v_{Bmim(PF_6)}} = \frac{\varepsilon_{H_2O}\eta_{Bmim(PF_6)}\left(\zeta_{DNA}^{H_2O} - \zeta_W^{H_2O}\right)}{\varepsilon_{Bmim(PF_6)}\eta_{H_2O}\left(\zeta_{DNA}^{Bmim(PF_6)} - \zeta_W^{Bmim(PF_6)}\right)} \quad (3)$$

where ε is the dielectric constant of the electrolyte, η the viscosity of the electrolyte, ζDNA and ζw the zeta potentials on DNA and pore surfaces respectively in corresponding electrolytes. In the absence of electroosmotic flow this expression simplifies, and by measuring the ζDNA in 2M aqueous KCl solution and in BmimPF$_6$ using phase analysis light scattering (Zetasizer Nano instrument Malvern Ltd., U.K.) retardation factor of 2120 is obtained and is predominantly due to the increase in the viscosity and decrease in the relative dielectric constant in the viscosity gradient system.

Figure 8:
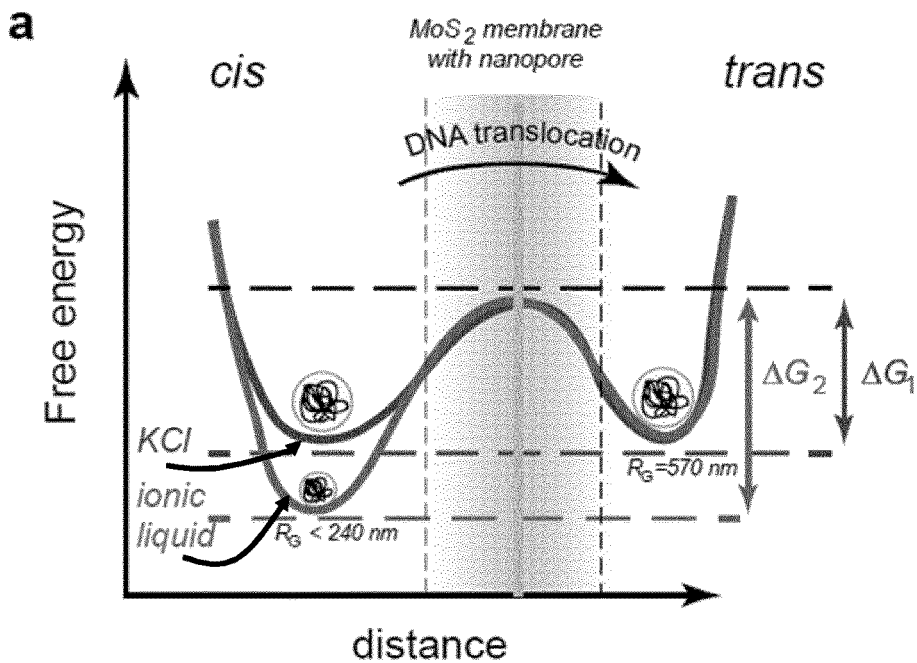
FIG. 8 shows a single molecule DNA translocation through a nanopore probes dynamics of Kramer's theory; a) Schematic representations of single-well free-energy surfaces, for two conditions. The schematics describes intrinsic (i.e. zero voltage) free-energy surface with a well and a barrier to translocation. In the context of the voltage-driven translocation of individual DNA molecules in a nanopore, the well of the free-energy surface corresponds to the random coil DNA configuration in a cis chamber with corresponding radius of gyration, while escape over the barrier involves translocation through the nanopore and subsequent adoption of random coil conformation. The free energy should include at least two parts, one from the phase transfer as described using L-J equation, another from entropy part of the DNA coil, but both of these two energy parts give a similar phase as drawn. (the difference is the distance and free energy level); b) Dependence of the translocation dwell time on the applied voltage for pNEB DNA in ionic liquid/KCl solution (dots) and in KCl/KCl (square). For both conditions exponential dependence reveals that translocation is voltage-activated. Lines are exponential fits to the data.
Figure 8:
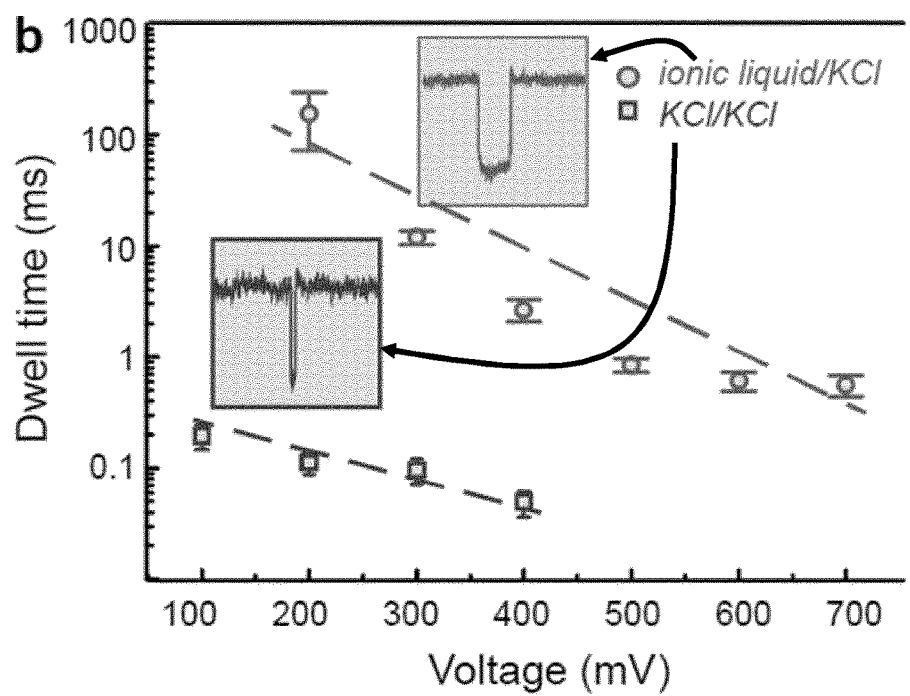

In general, single molecule DNA translocation process can be viewed as voltage driven over the barrier. In FIG. 8a, free-energy surface is schematized with a well and a barrier to translocation for viscosity gradient system and for the 2M KCl aqueous solution. In viscosity gradient system, λ-DNA adopts random coil configuration with gyration radius 240 nm, while in 2M KCl aqueous solution corresponding gyration radius is 570 nm. From the schematics, for applied voltage smaller than the free energy barrier associated with the translocation process, one can expect low probability of translocation since they are only diffusion driven. On the other hand, increasing the applied voltage reduces the effective barrier, and therefore significantly increases the probability of translocation. For the same pore, when working in the 2M KCl aqueous solution translocations start to be observed at much lower voltage 100 mV compared to viscosity gradient system (200 mV) as shown in FIG. 8b. This observation led to schematize higher energy barrier for the viscosity gradient system. FIG. 8b details the comparison between translocation times of pNEB DNA for a wide range of applied voltages and two different electrolyte systems (2M KCl aqueous solution and viscosity gradient system). DNA translocation in both systems obeys a power-law scaling:

$$\tau \sim V^\alpha \quad (4)$$

where τ is dwell time while V is the ionic voltage applied to the electrodes 11a and 11b (FIG. 1). For both conditions, exponential dependence was observed that reveals that translocation is voltage-activated. Lines are exponential fits to the data. Having established how the external potential affects the translocation dynamics in the viscosity gradient system, its scaling with DNA length was further investigated. The dependence of translocation time on DNA length was defined by Storm et al. 2005, Nano Lett 5, 1193-1197 by using force balance between the electric force in the nanopore and the viscous drag over the entire molecule. When adapting this model to the viscosity gradient system described herein as described in Example 3, the dependence of translocation time on DNA length can be derived as follows:

$$\tau_{RTIL} \sim \frac{3\pi\eta_{IL}L_0^{2\nu}}{qE} \quad (5)$$

where η is the viscosity of the solution, ν is the Flory index, while q is the charge density and L the DNA length. To validated the above expression, translocation times of λ DNA HindIII digest (564 bp, 2027 bp, 2322 bp, 4361 bp, 6557 bp, 6557 bp, 9416 bp and 23130 bp) was measured as a function of their length. Next, translocation experiments were conducted with λDNA and plasmid pNEB. From FIG. 9a, it is possible to identify respective dwell time for each fragment. In contrast to previous reports, where temporal dynamics has been DNA length dependent (Wananu et al., 2008, Biophys. 1, 95, 4716), temporal dynamics in the present system is independent on the DNA length, even slightly stronger for the longer DNA molecules, which is an ideal condition for DNA sequencing. FIG. 9b shows a clear power-law scaling of the dwell-time with the contour length of the DNA fragment while a least-squares fit to the data yields v=1.23 Flory exponent consistent to the theoretical prediction and previous experimental results obtained in water (v=1.26-1.27) (Storm et al., 2005, Nano Lett., 5, 1193). Finally, short oligonucleotides poly (dA) 30 (FIG. 11), poly (dT) 30, poly (dG) 30 and poly (dC) 30 were translocated through pores smaller than 3 nm.

Altogether, these results support that DNA translocation can be regulated to meeting single base time resolution through the use of device of the invention where a viscosity gradient is created between the first chamber portion and the second chamber portion. Such a viscosity gradient system can be not only used in standard ionic sensing experiment (ionic circuit only) but it can be combined with other kind of nanopore sensing such as transverse current signal detection. The use of the ultrahigh viscosity of ionic liquids in the first chamber portion allows controlling DNA translocation at room temperature.

According to one aspect, a system according the invention may be useful for example for DNA, RNA sequencing and detection of DNA methylation, low weight biomolecule detection, e.g. micro RNA, si RNA and detection of any low molecular weight biomarkers for early diagnosis (e.g. cancer etc.).

The invention having been described, the following examples are presented by way of illustration, and not limitation.

EXAMPLES

Example 1: Preparation of a Sensing Device of the Invention

The 20 nm thick supporting $SiN_x$ membranes are manufactured in a standard procedure using anisotropic KOH etching. Membrane sizes vary from 10 to 50 μm depending on the size of the backside opening. Electron beam lithography (EBL) and reactive ion etching (RIE) is used to make a square-shaped opening with a size of 200-500 nm on the membrane. $MoS_2$ flakes are first mechanically exfoliated onto substrates with 270 nm $SiO_2$ and fiducial markers. Optical microscope (Olympus IX51) was used to identify few layers or even monolayer flakes by their optical contrast. The thickness of chosen flakes is further confirmed by AFM measurements (Asylum Research Cypher). The method of transferring flakes to the square-shaped opening located on the $SiN_x$ membrane is similar to the widely used graphene transfer method. Electron beam drilling is performed in a JEOL 2200FS TEM operated at an acceleration voltage of 200 kV. Before loading in the microscope, the samples are annealed at 400° C. under a $H_2/Ar$ flux in order to remove any residual organic material left on the surface from the microfabrication processing and prevent hydrocarbon deposition. The fabrication process is detailed in Example 2. Membranes are imaged in the TEM mode with low magnification (<10 kx) in order to identify the location of suspended $MoS_2$ flake. Drilling is performed by focusing the beam with the condensor lens aperture (CLA) at high magnification (600 kx to 1 Mx). The nanopore membrane chip is mounted inside custom flow cell as soon as possible after drilling, otherwise stored in a desiccator with controlled humidity. After mounting the sample in the microfluidic setup, the wetting of the pore is facilitated by flushing the microfluidic system with a water-ethanol (v/v, 1:1) solution. It is crucial to inspect and remove bubbles trapped in the microfluidic channels. An Axopatch 200B patch clamp amplifier (Molecular Devices, Inc., Sunnyvale, Calif.) is used to record the ionic current in the single cell configuration with a sampling rate of 100 kHz and lowpass filter of 10 kHz. A NI PXI-4461 card was used for data digitalization and custom-made Lab View software for data acquisition. Chlorinated Ag/AgCl electrodes are inserted in both cis and trans reservoirs and connected to the Axopatch 200B. DNA samples (pNEB193, plasmid 2.7 kbp, New England; λ-DNA, 48 kbp, New England) are buffered with filtered and degassed 2 M KCl, 10 mM Tris, 1 mM EDTA and pH 7.4 and adjusted to a final concentration of 1-10 ng/μL. Finally, the solution containing DNA is injected into the cis chamber of the flow cell, which is grounded using the Ag/AgCl electrode. Each type of DNA is translocated in at least two different devices and representative and reproducible results and analysis are presented. Data analysis is performed offline using a custom open source Matlab code, named Open-Nanopore (http://lben.epfl.ch/page-79460-en.html), for event detection. Results are presented under FIGS. 2 to 4.

Example 2: Active Layer Preparation

Figures 10, 11:
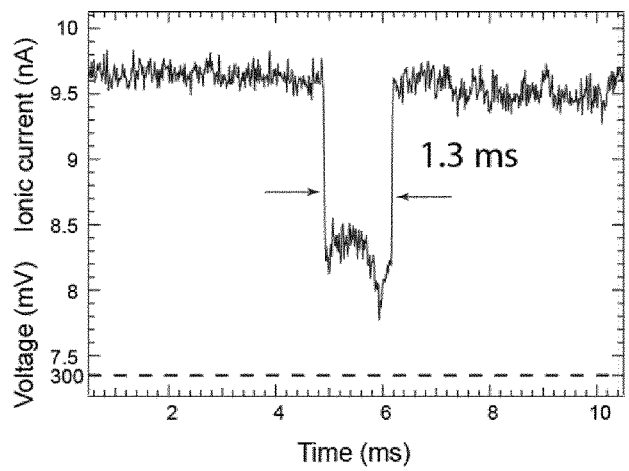
FIG. 10 shows a schematic representation of process steps of preparation of an active layer according to the invention.
FIG. 11 is a representative translocation event of poly(A) 30 in the gradient configuration biased at 300 mV, where cis-chamber is filled with IL and trans-chamber is filled with 2 M KCl. Dry poly(A)30 oligonucleotide is dissolved in IL. A 1.5 nm $MoS_2$ nanopore, calibrated from its ionic conductance, is used. To reduce the noise the device has been cured with PDMS. We observe trace as longer than 1 ms and conductance drops for ssDNA of ~5 nS.

Samples were prepared starting from boron-doped 380-μm-thick silicon chips (Ø100 mm) with resistivities of 20-30 Ohm*cm. Chips were coated on both sides with a 60-nm-thick layer of $SiO_2$ and a 20 nm top layer of low-stress $SiN_x$ (FIG. 10 a-c). The thickness of the $SiN_x$ was chosen for structural reasons, and the thickness of the $SiO_2$ was chosen to optimize the visibility of the 2D materials, enhancing the optical contrast with the bare. A square window (~500 μm×500 μm FIG. 10d-e) was opened in the $SiO_2/SiN_x$ layer on the back side by EBL and RIE. Chips were then wet etched in KOH to remove the silicon and the front side $SiO_2$ layer, resulting in a square $SiN_x$ membrane (~20 μm×20 μm (FIG. 10f). Before depositing 2D material on the chip, the substrate was pre-patterned using EBL, opening of 200-500 nm×200-500 nm square in a methyl methacrylate (MMA)/PMMA electron-beam resist double layer. The square is located in the center of the nitride membrane. A subsequent RIE process was used to create small opening in the membrane, as shown in (FIG. 10g) 2D membranes can be formed either using exfoliated single layer flakes or CVD grown material. Exfoliated 2D material flakes (preferably from dichalgonenides, or graphene) are first mechanically exfoliated onto substrates with 270 nm $SiO_2$ and fiducial markers (FIG. 10h). Next we use optical microscope (Olympus IX51) to identify few layers or even monolayer flakes by their optical contrast. The thickness of chosen flakes is further confirmed by AFM measurements (Asylum Research Cypher) FIG. 2. The method of transferring flakes to the square-shaped opening located on the $SiN_x$ membrane is similar to the widely used graphene transfer method (FIG. 10i).

Graphene CVD

Large-area graphene films were grown on copper foils. The growth took place under the flow of a methane/argon/hydrogen reaction gas mixture at a temperature of 1,000° C.

At the end of the growth, the temperature was decreased rapidly and the gas flow turned off. The copper foils were then coated with poly(methylmethacrylate) (PMMA) and the copper etched away, resulting in a centimetre-scale graphene film ready to be transferred onto the chips with membranes. This graphene was single layer, continuous and had good electronic properties.

Molybdenum Disulfide CVD

Single layers (SL) $MoS_2$ have been grown by chemical vapour deposition (CVD) on sapphire c-plane (FIG. 10h). Substrates were cleaned by sonication in acetone, isopropanol and DI-water, consecutively, followed by 1 h etching in $H_2SO_4$:$H_2O_2$ (3:1). They were then loaded into a 2-inch CVD furnace and placed face-down under over a crucible containing 5 mg $MoO_3$ (≥99.998% Alfa Aesar) with another crucible containing ~350 mg of sulfur (≥99.99% Aldrich) located upstream. The CVD growth is performed at atmospheric pressure with flowing ultrahigh-purity argon. The growth recipe is following: set 300° C. with 200 s.c.c.m. for 10 min, ramp to 700° C. at 50° C. $min^{-1}$ with 10 s.c.c.m., set 700° C. for 10 min, cool to 570° C. with 10 s.c.c.m., open furnace and flow 200 s.c.c.m. for rapid cooling.

Electron beam drilling is performed in a JEOL 2200FS TEM operated at an acceleration voltage of 200 kV. Before loading in the microscope, the samples are annealed at 400° C. under a $H_2$/Ar flux in order to remove any residual organic material left on the surface from the microfabrication processing and prevent hydrocarbon deposition. Membranes are imaged in the TEM mode with low magnification (<10 kX) in order to identify the location of suspended $MoS_2$ flake. Drilling is performed by focusing the beam with the condensor lens aperture (CLA) at high magnification (600 kX-1 MX) resulting in pores that can have diameters from 1 nm-20 nm (FIG. 10j-k).

Example 3: Molecular Sensing Device with Viscosity Gradient

Exfoliated or CVD grown $MoS_2$ thin layers were transferred either from $SiO_2$ or sapphire substrates and suspended on the SiNx membranes, and nanopores were further drilled using a JEOL 2200FS high resolution transmission electron microscope (HRTEM) as described in Liu et al. (in press). The chips with nanopore were sealed by silicone o-rings between two polymethylmethacrylate (PMMA) chambers as reservoirs. After mounting, the whole flow cell was flushed with H2O:ethanol (v:v, 1:1) solution and wetted for at least 30 mins. Then, 2 M KCl solution buffered with 10 mM Tris-HCl and 1 mM EDTA at pH 7.0 and $Bmin^+PF6^-$ (Aldrich-Sigma) as RTIL were injected to perform current-voltage (IV) characteristics measurements as shown on FIG. 5. A pair of chlorinated Ag/AgCl electrodes immersed in two reservoirs and connected to a Axopatch 200B patch clamp amplifier (Molecular Devices, Inc. Sunnyvale, Calif.) that was used to measure ionic current as a function of time, namely, Ii(t). For detection of the homopolymers of short nucleotides, and when working with the small pores <5 nm we employed Chimera preamplifier (Chimera Instruments, New York, N.Y., USA). The device was running at the applied voltage for at least 1 hr to perform blank experiments. DNA samples were diluted to pure $Bmin^+PF_6^-$ by mixing 10 λ L DNA stock solution with $Bmin^+PF_6^-$. DNA samples (pNEB193, plasmid 2.7 k bp, New England λ-DNA, 48 k bp, New England) as described in Table 1 below were purchased from commercial supplier, aliquoted and stored at -20° C. before the use. NI PXI-4461 card was used for data digitalization and a custom-made LabView 13 software for data acquisition. The sampling rate is 100 k Hz and a built-in low pass filter is used. Data analysis is performed offline using a custom open source Matlab code, named OpenNanopore (Raillon et al., 2012, supra) (http://lben.epfl.ch/page-79460-en.html), for event detection. Each type of DNA is translocated in at least two different devices, and representative and reproducible results and analysis are presented.

TABLE 1

| DNA | Length (bp, nt) | Supplier |
| --- | --- | --- |
| lambda | 48502 | New England Biolab |
| Lambda HindIII | 564, 2027, 2322, 4361, 6557, 6557, 9416, 23130 | New England Biolab |
| pNEB 192, plasmid | 2700 | New England Biolab |
| poly A30, T30, G30, C30 | 30 | Microsynth |
| single nucleotides | 1 | Sigma |

COMSOL Modeling

Numerical solutions were performed using the COMSOL 4.2 Multiphysics finite element solver in 3D geometry, imposing a cylindrical symmetry along the axis of the nanopore. The full set of Poisson-Nerst-Planck (PNP) equations were solved, with the boundary conditions at the $MoS_2$ corresponding to idealized, uncharged membrane impermeable to ions. Simulated $MoS_2$ conductances in 2M aqueous KCl solution, viscosity gradient system and pure RT ionic liquid ($Bmin^+PF_6$) was found to differ by <5% from the measured values presented in FIG. 2c. A DNA molecule was modeled as a 50 nm long stiff insulating rod threading the nanopore along its axis.

Force Balance Model

The Stokes drag force in the pores >5 nm DNA-pore interactions can slow down DNA translocation in sub-5 nm pores, while in the larger pores those interactions are negligible, consequently in the pores >5 nm those interactions should not contribute to the DNA retardation. In solution, long DNA molecule forms random coil, thus the viscous drag of the whole DNA molecule then can be estimated as, $$F_{drag} = 6\pi \eta v_{DNA} R_g \qquad (6)$$

where Rg is the radius of gyration, η is the solvent viscosity, and vDNA is the linear velocity of DNA translocation. As the polymer threads through the pore, the center of mass of this sphere moves toward the pore at a velocity, $$v_{DNA} = \frac{dR_g}{dt} \qquad (7)$$

Therefore, the Stokes drag force can be written as, $$F_{drag} = 6\pi \eta_{IL} R_g \frac{dR_g}{dt} \qquad (8)$$

If we assume that DNA translocation velocity is constant, which implies that the force balance between driving force and Stokes drag force is met at all times, i.e. from the first monomer translocation to the final monomer translocation. Then, velocity can be expressed $$v = \frac{R_g}{\tau} \qquad (9)$$

where τ is the whole chain translocation time, in the experiments denoted as translocation dwell time. As proposed by Storm et al., 2005, supra, the principal effect of hydrodynamics is to resist motion with a hydrodynamic drag Stokes drag on the DNA coil.

$$F_{Drag} = F_{Driving} \quad (10)$$

In the present case, $$qE = 6\pi\eta R_g \frac{R_g}{\tau} \quad (10)$$

we obtain, $$\tau = \frac{6\pi\eta}{qE} R_g^2 \quad (11)$$

Figure 9:
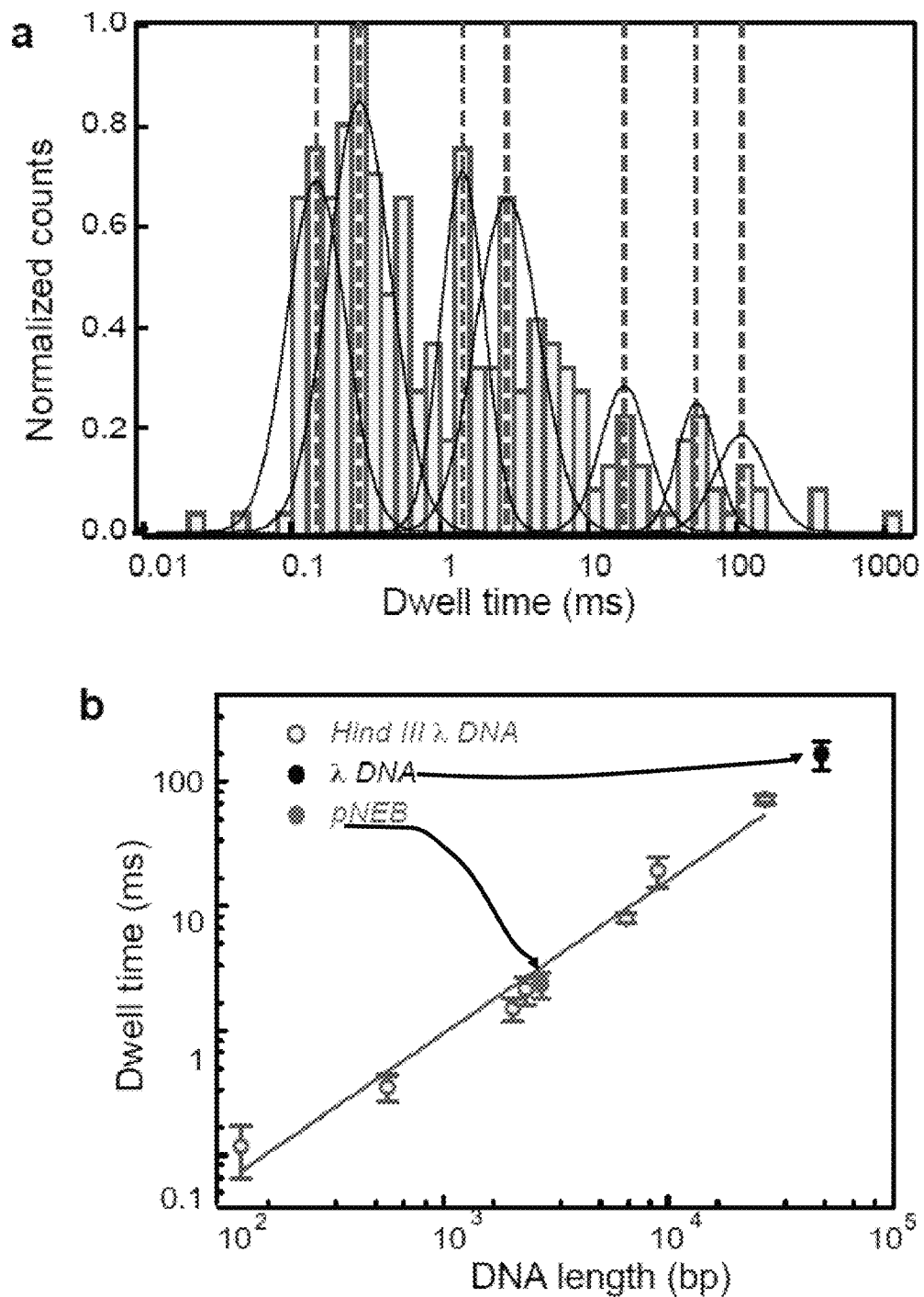
FIG. 9 shows the dependence of the translocation dwell time on the DNA length in a device configuration with a viscosity gradient system as described in Example 3; a) Event distribution of k DNA HindIII digest (564 bp, 2027 bp, 2322 bp, 4361 bp, 6557 bp, 6557 bp, 9416 bp and 23130 bp) translocations in viscosity gradient system; b) Log-log plot of DNA translocation timescales as a function of DNA length (bp) measured using a 20-nm $MoS_2$ pore. Besides k DNA HindIII digest, pNEB and k DNA were added. The line shows the result of a power-law fit to the data, all data points which follow a power law fit exponent of 2v=1.23.

Due to the fractal nature of DNA polymers, the equilibrium relation between $R_g$, the radius of gyration of the polymer and DNA length $L_0$ is best described by $Rg=L^\nu$. Then, expression lithe whole chain translocation time can be written $$\tau \sim \frac{6\pi\eta}{qE} L_0^{2\nu} \quad (12)$$

where ν is the Flory exponent. Experimentally we find $\tau \sim L_0^{1.23}$, as shown in FIG. 9, validating that room temperature ionic liquid BmimPF$_6$ is a good DNA solvent. For the present viscosity gradient system, we only consider the biggest contribution to the Stokes drag force which originates form the drag of the DNA coil in the cis chamber since viscosity of RTIL is much higher than water. Then, $$F_{drag} = 6\pi\eta_{IL} R_g^{cis} \frac{dR}{dt} \quad (13)$$

Where $$R_g^{cis}(t) = ((N-n)b)^\nu \quad (14)$$

where N is the total number of DNA monomers while n is the monomer number in the trans chamber and b corresponds the monomer number length $$F_{drag} = 6\pi\eta_{RTIL}(N-n)^\nu b^\nu \nu b^\nu (N-n)^{\nu-1} \frac{dn}{dt} \quad (15)$$

Introducing the force balance, $$qE = 6\pi\eta_{RTIL}(N-n)^\nu b^\nu \nu b^\nu (N-n)^{\nu-1} \frac{dn}{dt} \quad (16)$$

$$\int_0^\tau qE dt = \int_0^N 6\pi\eta_{RTIL}(N-n)^\nu b^\nu \nu b^\nu (N-n)^{\nu-1} dn \quad (17)$$

For the viscosity gradient system, $\tau_{RTIL}$ chain translocation time can be written $$\tau_{RTIL} \sim \frac{3\pi\eta_{IL} L_0^{2\nu}}{qE} \quad (18)$$

At this point we can introduce retardation factor that allow us to compare between DNA translocation well times obtained aqueous 2M KCl solution and in the viscosity gradient system can introduce retardation factor that allow us to compare between DNA translocation well times obtained aqueous 2M KCl solution in and in the viscosity gradient system $$r = \frac{\tau_{RTIL}}{\tau_{H_2O}} = \frac{\eta_{RTIL}}{2\eta_{H_2O}} \quad (19)$$

We therefore obtain a retardation factor higher than 200 that is predominantly due to the increase in the viscosity in the viscosity gradient system.

Example 4: Identification of Single Nucleotides in a Molecular Sensing Device with Viscosity Gradient To exploit the full potential of the viscosity gradient system described above, single nucleotides dAMP (Deoxyadenosine-5'-Monophosphate), dTMP (Deoxythymidine monophosphate), dGMP (Deoxyguanosine monophosphate) and dCMP (Deoxycytidine monophosphate). Exceptional durability of the MoS$_2$ nanopore allowed has allowed 8 experiments with 500-3,000 events per experiment (FIG. 12) using the same pore. Each experiment has been preceded with the flushing of the fluidics and with the short control experiment to establish the absence of the analyte from the previous experiment. Not only does this show the extraordinary resilience of the nanopores, but, also single nucleotide dwell times were comparable to the translocation times of 30 mer homopolymers. At this scales, when working with 3 nm nanopores in single-layer MoS$_2$ and when comparing translocation times of single nucleotides to homopolymers one needs to account for the charge differences that will result in the lower net force acting on the single nucleotide compared to the homopolymers. The use of single-layer MoS$_2$ as membrane material, viscosity gradient system in combination with the small nanopore has been crucial for the single nucleotide discrimination shown in FIG. 12.

Figure 12:
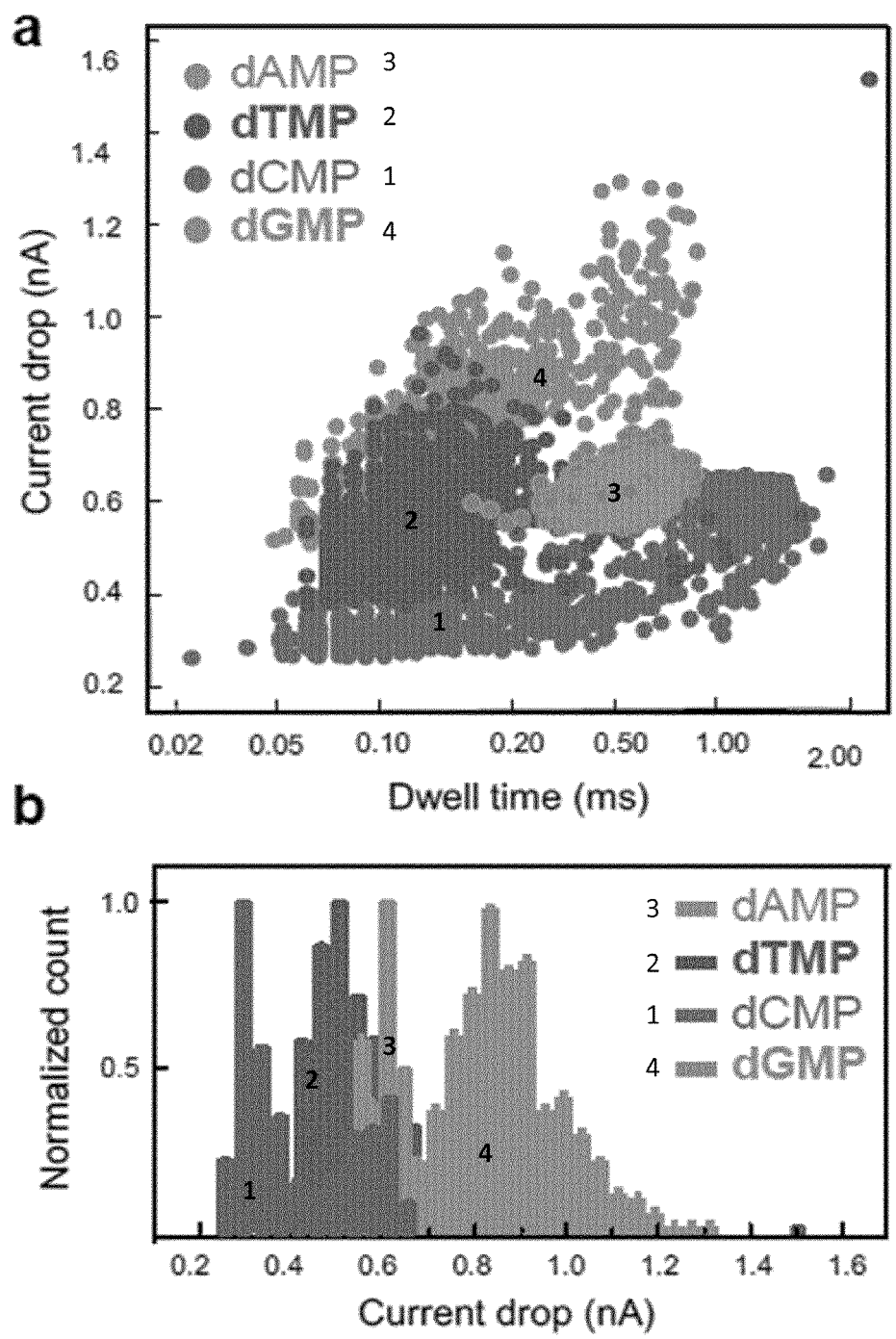
FIG. 12 is a representation of translocation events of the four single nucleotides (dAMP, dTMP, dGMP and dCMP) in a gradient configuration biased at 200 mV, as described in Example 4. (a) Scatter plots of nucleotide translocation events, showing distinguished current drops and dwell times for dAMP, dCMP, dTMP, and dGMP. (b) Normalized histogram of current drops for dAMP, dTMP, dCMP, dGMP. (c)
Figure 12:
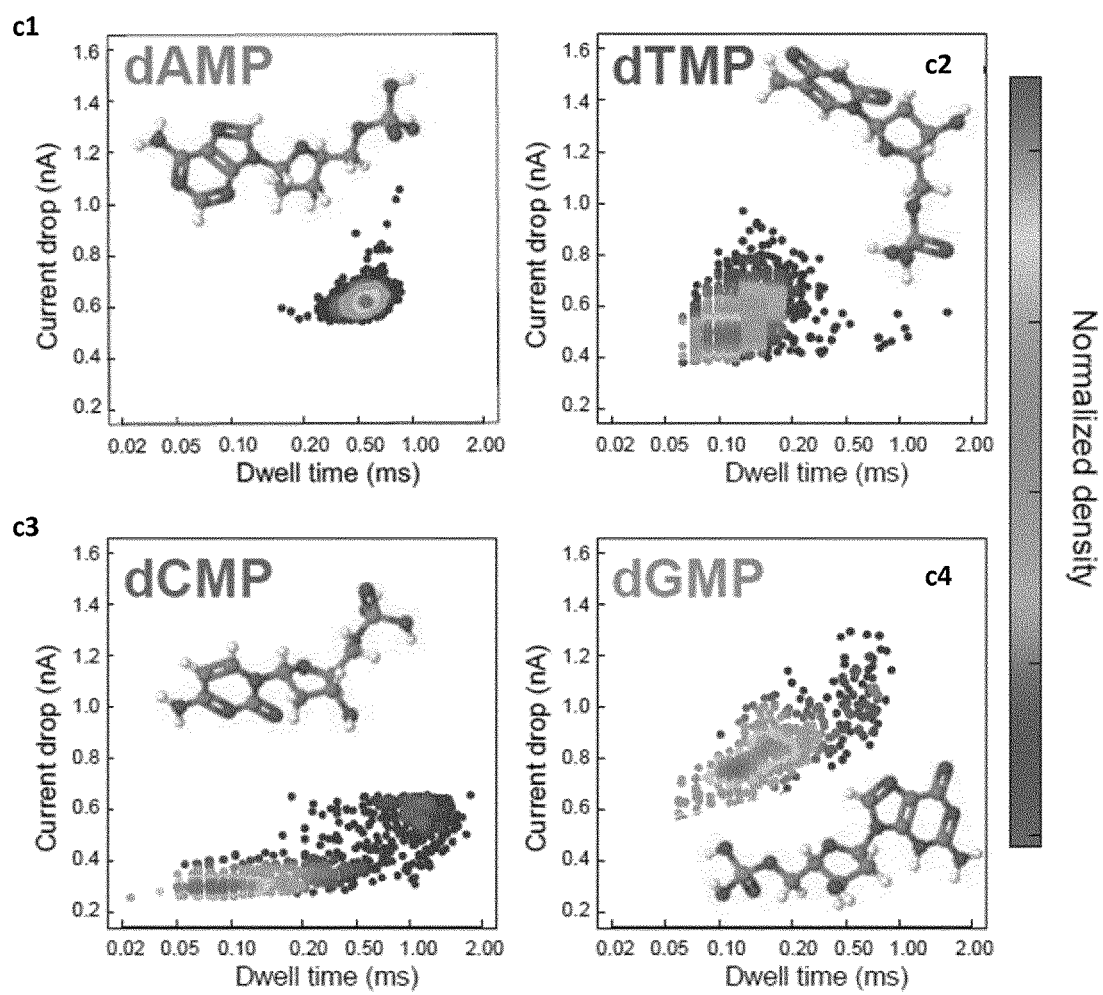

The obtained translocation speed is in the range from 1-50 nucleotide/ms. In accordance with the single nucleotide size, the biggest current drop was observed for dGMP, centered at 0.8 nA and the smallest current drop for the smallest single nucleotide dCMP, 0.3 nA (FIG. 12). These observations are in good agreement with the results obtained on single nucleotide discrimination using protein pores (Clarke et al., 2009, supra). Although the current drop for dAMP is slightly larger than dTMP (0.65 nA compared to 0.45 nA), it is believed that this originates from the stronger Bmim+affinity towards dAMP compared to dTMP. It has been established that RTILs could selectively bind to DNA (Chandran et al., 2012, *Journal of the American Chemical Society*, 134: 20330-20339), while RTILs based on metal chelate anions could be designed to have specific bonding to the bases and this property could be further exploited to amplify the small differences in bases.

Using the only ionic current drops of 500-3,000 events for four nucleotides, Welch's t test was performed and p-values were all less than 0.0001. Moreover this simple statistical analysis revealed a minimum event number to be 6-9 for nucleotide identification with a confidence of 99%. With the addition of the other parameters such as dwell time, it might be possible to identify single nucleotide with one read and the presence of a direct band gap in $MoS_2$ should allow for straightforward device multiplexing.

All those data show that a device sensing according to the invention allows regulating DNA translocation speed through solid-state nanopores to meet the requirements for achieving single base time resolution. The force balance model detailed in Example 3 provides a mechanism to explain dependence of the translocation dwell time on the DNA length and offers a route for experimental measurement of polymer exponent index. Above force balance model calculations are dependent on the number of DNA segments and those data show that the sensing system allows the detection of short homopolymers and single nucleotides to reach the single-base limit. The viscosity gradient system can be combined with other schemes of nanopore sensing such as transverse current signal detection. Owing to the ultrahigh viscosity of ionic liquids, the DNA translocation can be well-controlled at room temperature.

Therefore, the use of ionic liquids and an active layer of semi-conducting material such as a monolayer $MoS_2$ having at least one nanopore combined with transverse current detection in a molecular sensing device of the invention might reach all necessary requirements for DNA sequencing such as optimal time resolution and signal resolution. This configuration, when combined with the platform described in (Traversi et al., 2013, *Nat. Nanotechnol.*, 8, 939-945) that allows multiplexing should allow reducing costs relating to sequencing and enhancing the signal statistics.

Example 5: Example of a Mixture of RTILs of the Invention where Viscosity can be Adjusted In order to adjust precisely the viscosity of the first conducting liquid comprising a RTIL of the invention, thermal regulation of the first chamber portion containing a first conducting liquid comprising a RTIL of the invention was regulated by a temperature element system comprising a Peltier element allowing thermoelectric regulation within ±0.1° C. and fast thermal equilibration within the first chamber portion. As shown on FIG. 14A, viscosity of the pure RTIL (Bmim(PF6) or Bmim(PF4) can be significantly changed over a range of between 50-300 mPa s when temperature is varied from 20 to 18° C. In addition, as shown on FIG. 14B, by mixing pure Bmim(PF6) and pure Bmim (PF4) at different compositions over a range of mass ratios Bmim(PF6) to Bmim(PF4) from 0 to 1 (0, 0.15, 02, 0.3, 0.4, 0.5, 0.6, 0.7, 0.8, 0.9 and 1) at room temperature, one can also alter viscosity of the RTIL mixture over a range of 300-180 mPa s as shown in Khupse et al., 2010, *Bio-Inorganic Physical Theoretical & Analytical Chemistry*, 49, 727.

Example 6: Identification of Nucleotide Strings in a Molecular Sensing Device with Viscosity Gradient Besides deoxynucleotide triphosphate differentiation and detection of short nucleotides as shown in Example 4, sequencing of nucleotide three-mers up to six-mers was carried out by a sensing device of the invention where the first conducting liquid consisted in a pure RTIL ($BminPF_6$) and the second conducting liquid was 100 mM KCl, 25 mM Tris HCl, pH 7.5. The support layer was made in $MoS_2$ and experiment was carried out as described in Example 4 using a 0.7-2 nm thick and 1-4 nm large nanopore. A transmembrane bias voltage of +200 mV was set. The three-mers concentration in RTILs was 5 μg/ml. It was possible to detect and identify sequences of nucleotide up to six-mers with a reasonable signal to noise ratio higher than 10. As an example, FIG. 14 displays translocation events (A) as measured by variations of the ionic current while the molecular analyte in the form of the tree-mers CGC, GCG and CC translocate through the nanopore and the current drops obtained for single nucleotides in combination with the expected signal shape in the absence of the noise allow for the specific identification of the sequences of the thro three-mers. Comparable data were obtained for nucleotide six-mers. Altogether those results support that a sensing device of the invention is able to precisely identify the sequence of each single nucleotide in a string of nucleotide and can be usefully used in the sequencing of molecular analyte such as nucleotides or amino acids.

Figure 2:
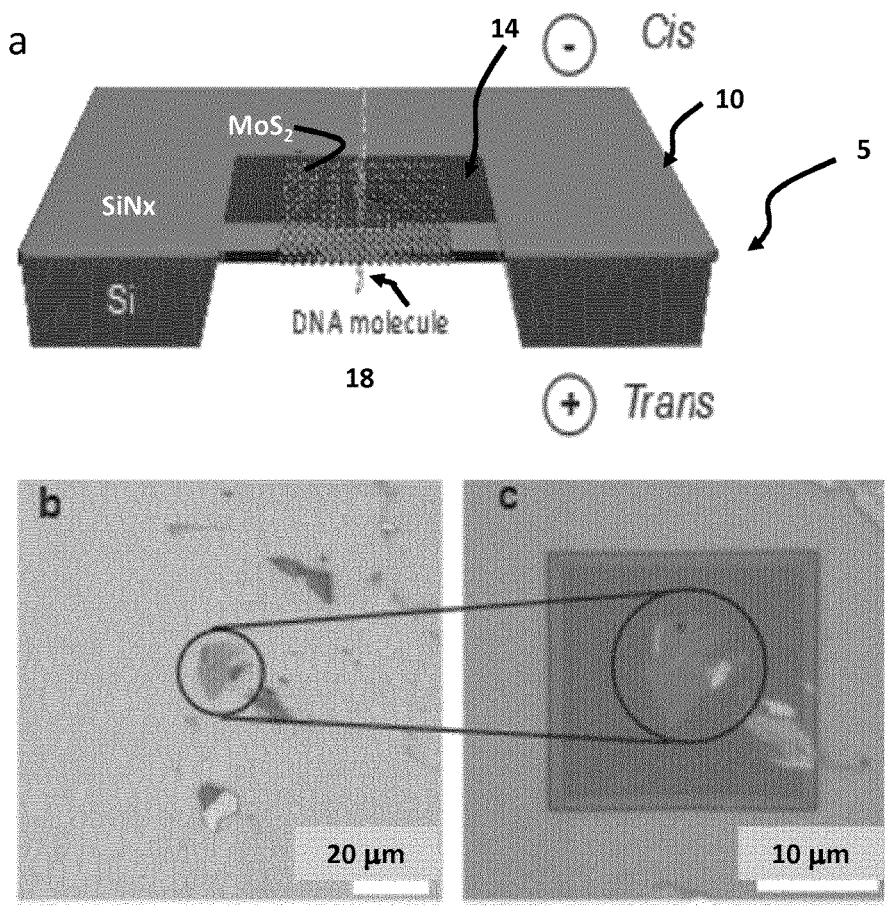
FIG. 2 is an illustration of a molecular sensing system according to an embodiment of the invention in a configuration as described in Example 1. a) Schematic illustration of an active layer according to the invention made of $MoS_2$ for DNA translocation. Monolayer MoS2 is suspended on a $SiN_x$ support layer that separates two reservoirs containing buffered potassium chloride. Electrical field is applied by a pair of Ag/AgCl electrodes to drive DNA molecules passing through a nanometer size pore on $MoS_2$, while ionic current through the pore is recorded using an Axonpatch low-noise amplifier; b) Optical image of a freshly exfoliated monolayer $MoS_2$ flake (marked with the black circle) exhibiting minimum contrast with respect to the $SiO_2$ substrate; c) Optical image after the chosen flake has been transferred from the $SiO_2$ substrate to the desired location (a square-shaped opening made by EBL and RIE) on the $SiN_x$ support layer; d1) AFM image of the chosen flake in b) and d2) Height profile is taken from the white line in the image in d1), showing a 9 Å height difference between the surface and the $MoS_2$ flake; e) Low-magnification TEM image of a $MoS_2$ flake fully covering the opening in the $SiN_x$ support layer marked with the black circle. The edge of this flake is clearly seen in the upper part of the image. (f-i) High resolution TEM images of nanopores with various sizes drilled by a focused electron beam. The lattice of $MoS_2$ is visible under such a magnification (1 MX).
Figure 2:
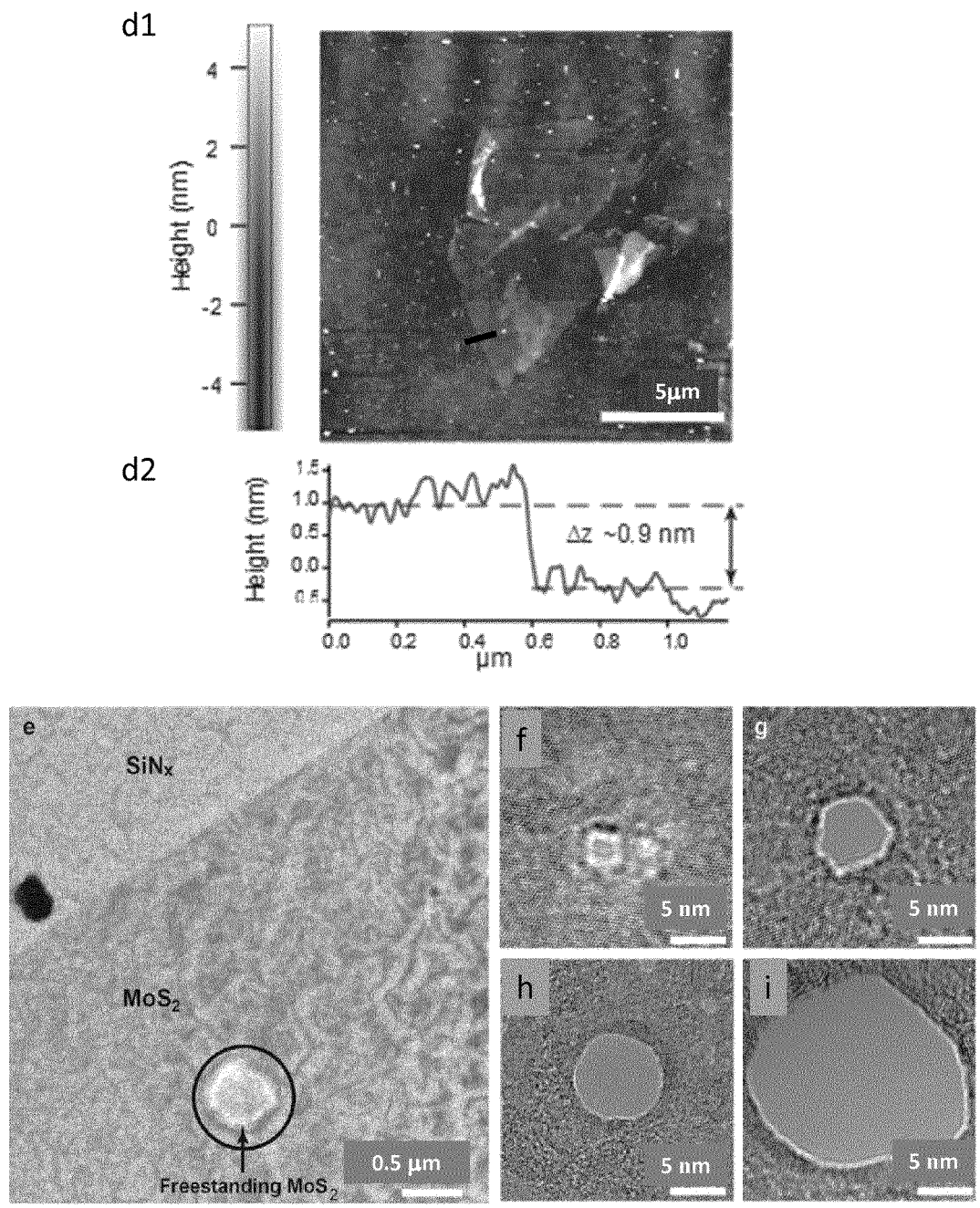

LIST OF ELEMENTS REFERENCED (FIGS. 1 and 2)

1 molecular sensing system
  2 housing
    3 sensing chamber
      3a first chamber portion (cis chamber portion)
        16a temperature regulation system
        temperature sensing element
        heating/cooling member
      3b second chamber portion (trans chamber portion)
        16b temperature regulation system
        temperature sensing element
        heating/cooling member
      temperature regulation system
  5 sensing device
    6 active layer
      →semi-conducting
    12 pore(s) (nano)
      Dp pore diameter
      Hp active layer thickness
    10 support layer(s)
      14 support layer orifice
      Ds support layer orifice diameter
      Hs support layer thickness
    15 support layer end section
  7 signal processing circuit
    8 ionic current circuit
      $V_B$ voltage source
      $A_i$ ionic current measuring system
        $I_i$ ionic current
      11a, 11b electrodes
    9 transverse current circuit
      $V_T$ voltage source
      $A_t$ transverse current measuring system
        $I_t$ transverse current
    20 transverse current amplifying system
      13b, 13c1 electrical terminals
      21 semi-conducting element
      $V_{DD}$ voltage source
    13 electrical terminals (13a, 13b)
    Connection interface to computing and user interface system
  4 electrically conducting liquid
    4a first conducting liquid
      →room temperature ionic liquid (RTIL)
    4b second conducting liquid →aqueous liquid with electrolyte (KCl) (ionic buffer)

18 molecular analyte

The invention claimed is:

1. A molecular sensing system including:
a sensing device (5) comprising at least one support layer (10), and an active layer (6) of a semi-conductive material mounted on said support layer and having at least one nano-pore (12) configured for translocation of a molecular analyte (18) therethrough;
an electrically conducting liquid (4) in contact with the active layer in a region around said at least one nano-pore; and
a signal processing circuit (7) comprising an ionic current circuit (8) configured to generate an ionic current (Ii) in the electrically conducting liquid influenced by the translocation of the molecular analyte through the at least one nano-pore,
wherein said electrically conducting liquid comprises a first conducting liquid (4a) on a first side of the active layer and a second conducting liquid (4b) on a second side of the active layer, the first conducting liquid having a viscosity (cP1) greater than a viscosity (cP2) of the second conducting liquid, wherein the first conducting liquid is selected from the group consisting of an essentially pure room temperature ionic liquid (RTIL), an RTIL mixed with at least one organic solvent, and a water-miscible RTIL mixed with water whereby the water content is less than 50 wt %,
wherein the support layer (10) comprises a support layer orifice (14), a diameter (Ds) of the support layer orifice being greater than a diameter (Dp) of the at least one nano-pore, whereby a portion of the active layer extends over said support layer orifice in a suspended manner, and wherein at least said portion of the active layer extending over said support layer orifice in a suspended manner is the semi-conductive material,
wherein the signal processing circuit (7) further comprises a transverse current circuit (9) configured to generate a transverse current (It) in the semi-conductive material and wherein cP1 at room temperature is from about 100 cP to about 500 cP.

2. The molecular sensing system according to claim 1, wherein the RTIL is selected from: (a) RTILs based on $AlCl_3$ and organic salts; (b) RTILs based on anions selected from $[PF_6]^-$, $[BF_4]^-$ and $[SbF_6]^-$; (c) RTILS based on anions selected from $[CF_3SO_3]^-$, $[(CF_3SO_2)_2N]^-$, and $[Tf_2N]^-$; and (d) RTILs based on anions selected from alkylsulfates and alkylsulfonates; and (e) carboranes and orthoborates.

3. The molecular sensing system according to claim 1, wherein the RTIL comprises hexafluorophosphate anions.

4. The molecular sensing system according to claim 1, wherein the RTIL comprises N,N-dialkylimidazolium cations.

5. The molecular sensing system according to claim 1, wherein the RTIL is 1-butyl-3-methylimidazolium hexafluorophosphate ($BminPF_6$).

6. The molecular sensing system according to claim 1, wherein the RTIL is a mixture of 1-butyl-3-methylimidazolium hexafluorophosphate ($BminPF_6$) and 1-butyl-3-methylimidazolium tetrafluoroborate ($BmimBF_4$).

7. The molecular sensing system according to claim 1, wherein the second conducting liquid is an aqueous liquid comprising an electrolyte.

8. The molecular sensing system according to c claim 7, wherein the electrolyte is potassium chloride (KCl).

9. The molecular sensing system according to claim 1, wherein the semi-conductive material comprises $MoS_2$.

10. The molecular sensing system according to claim 1, wherein the thickness of the active layer is in a range between 0.3 nm and 2 nm.

11. The molecular sensing system according to claim 1, wherein the diameter of the at least one nano-pore is smaller than 4 nm.

12. The molecular sensing system according to claim 1, further comprising a housing (2) comprising a sensing chamber (3) a first chamber portion (3a) containing the first conducting liquid (4a) and a second chamber portion (3b) containing the second conducting liquid (4b) and wherein said sensing chamber is thermoregulated by a temperature regulating element (30).

13. The molecular sensing system according to claim 1, wherein the ionic current circuit (8) is connected to a pair of Ag/AgCl electrodes coupled to the electrically conducting liquid on opposite sides of the active layer.

14. The molecular sensing system according to claim 10, wherein the thickness of the active layer is in a range between 0.7 nm and 1.4 nm.

15. The molecular sensing system according to claim 10, wherein the thickness of the active layer is about 1 nm.

* * * * *